US 8,558,003 B2

(12) United States Patent
Elmaleh et al.

(10) Patent No.: US 8,558,003 B2
(45) Date of Patent: Oct. 15, 2013

(54) IMAGING TRACERS FOR EARLY DETECTION AND TREATMENT OF AMYLOID PLAQUES CAUSED BY ALZHEIMER'S DISEASE AND RELATED DISORDERS

(75) Inventors: David R. Elmaleh, Newton, MA (US); Timothy M. Shoup, Waltham, MA (US); Alan J. Fischman, Boston, MA (US)

(73) Assignee: The General Hospital Corporation, Charlestown, MA (US)

( * ) Notice: Subject to any disclaimer, the term of this patent is extended or adjusted under 35 U.S.C. 154(b) by 0 days.

(21) Appl. No.: 12/854,625

(22) Filed: Aug. 11, 2010

(65) Prior Publication Data

US 2010/0298389 A1    Nov. 25, 2010

Related U.S. Application Data

(62) Division of application No. 12/110,686, filed on Apr. 28, 2008, now Pat. No. 7,858,803.

(60) Provisional application No. 60/924,053, filed on Apr. 27, 2007.

(51) Int. Cl.
*A61K 31/428* (2006.01)
*A61K 51/04* (2006.01)
*A61K 49/00* (2006.01)
*C07D 277/66* (2006.01)

(52) U.S. Cl.
USPC ......... 548/178; 514/367; 424/1.81; 424/1.85; 424/1.89; 424/9.1

(58) Field of Classification Search
USPC .................................. 548/156, 178
See application file for complete search history.

(56) References Cited

U.S. PATENT DOCUMENTS

| 4,933,156 A * | 6/1990 | Quay et al. ............. 424/1.85 |
| 6,696,039 B2 | 2/2004 | Kung et al. |
| 2004/0204344 A1 | 10/2004 | Huang |

FOREIGN PATENT DOCUMENTS

| WO | WO-2004/083195 | 9/2004 |
| WO | WO-2004/083195 A1 * | 9/2004 |
| WO | WO-2006/014382 | 2/2006 |

OTHER PUBLICATIONS

Siegemund, T., et al. "Thioflavins released from nanoparticles target fibrillar amyloid β in the hippocampus of APP/PS1 transgenic mice", Int J. Dev. Neurosci. 24:195-201 (2006).
International Search Report dated Oct. 21, 2008 for PCT/US2008/061742.

* cited by examiner

*Primary Examiner* — Laura L. Stockton
(74) *Attorney, Agent, or Firm* — Foley Hoag, LLP

(57) ABSTRACT

The present invention relates to compounds and methods for imaging and treating Alzheimer's disease or an amyloidosis-associated pathological condition that utilize a novel amyloid imaging tracer for detecting amyloid deposits in a subject suffering from these conditions. In certain embodiments, the invention relates to [N-2[18F]fluoropropyl]-2-(4'-(methylamino)-phenyl)-6-hydroxybenzothiazole (F-18MHT) and dimers thereof.

4 Claims, 5 Drawing Sheets

Figure 5

| Organ Affected | Possible Consequences |
|---|---|
| Brain | Alzheimer's disease |
| Heart | Heart failure, abnormal heart rhythms (arrhythmias), enlarged heart |
| Kidneys | Kidney failure; fluid accumulation in the tissues, causing swelling (edema) |
| Nervous system | Numbness, tingling, weakness |
| Digestive system | Intestinal obstruction, poor nutrient absorption, enlarged tongue |
| Blood and blood vessels | Easy bruising |
| Lungs | Difficulty breathing |
| Skin | Skin papules, bruises, enlarged lymph nodes |
| Thyroid gland | Enlarged thyroid gland |
| Liver | Enlarged liver |
| Musculoskeletal system | Carpal tunnel syndrome |
| Lymph nodes | Enlarged lymph nodes |

IMAGING TRACERS FOR EARLY DETECTION AND TREATMENT OF AMYLOID PLAQUES CAUSED BY ALZHEIMER'S DISEASE AND RELATED DISORDERS

RELATED APPLICATIONS

This application is a divisional application of U.S. patent application Ser. No. 12/110,686, filed Apr. 28, 2008, now U.S. Pat. No. 7,858,803, which claims the benefit of priority to United States Provisional Patent Application Ser. No. 60/924,053, filed Apr. 27, 2007; both of which are hereby incorporated by reference.

BACKGROUND

Millions of Americans suffer from dementia and other cognitive deficits as a result of Alzheimer's disease (AD), a neurodegenerative disease. Due to its occurrence in the brain, it is difficult to diagnose the condition and to determine its cause without dangerous brain biopsy. Scientists believe that as many as 4.5 million Americans suffer from AD. AD usually begins after age 60 and its risk goes up with age. The cause of AD is unknown and, at present, no cure has been found.

AD can only be definitely confirmed after an autopsy, which prevents early accurate diagnosis and treatment of the condition. Neuropathologically, AD is characterized by the presence of neuritic plaques, neurofibrillary tangles and neuronal loss. See *Mann. Mech. Ageing Dev.* 1985, 3(1), 213. Doctors can diagnose AD correctly up to 90 percent using several tools to diagnose "probable" AD, namely, (1) questions about the person's general health, past medical problems, and ability to carry out daily activities; (2) tests of memory, problem solving, attention, counting, and language; (3) medical tests, such as tests of blood, urine, or spinal fluid; and (4) brain scans.

Postmortem brain tissues of AD victims show the presence of amyloid cores of neuritic plaques that are composed of amyloid β-(A β-) protein being predominantly arranged in beta-pleated sheet configuration. See *J. Biol. Chem.* 1992, 267(24), 17082; and *Proc. Natl. Acad. Sci., USA* 1986, 83(2), 503.

Deposition of amyloid β-(A β-) protein occurs, however, not only in individuals that have AD, but it also frequent among individuals who are undergoing the aging process. Thus, it is very critical to distinguish the AP production due to the normal aging process or to AD or other dementia-causing diseases such as DLB dementia associated with Louis Body. In the normal aging process, non-compact or diffuse amyloid plaques containing less fibrillar AP are deposited primarily in the brain. In contrast, AD patients have brains that are characterized by an unanatomically widespread process of amyloid deposition and neurite plaque formation containing dense amyloid fibrils.

Clinical tests to determine the onset of AD and its progression are not presently sensitive and several agents are reported as potential PET and SPECT imaging tracers. Some of the developmental research on imaging agents useful for the diagnosis of AD and other related diseases are discussed below.

U.S. Patent Publication Application No. 2006/0018825 A1, assigned to BF Research Institute, hereby incorporated by reference, describes a series of BF compounds or a salt or solvate thereof that can be used as a probe for the imaging and diagnosis of diseases in which amyloid P-protein accumulates. These compounds have high specificity for diffuse plaques and act as early indicators of AD. In addition, they have rapid clearance from the brain.

Okamura et al. (in *J. Neurosci.* 2004, 24(10), 2535) describes a labeled sterylbenzoxazole derivative compound, $^{18}$F-radiolabeled 6-(2-fluoroethoxy)-2-[2-(4-methylaminophenyl)ethenyl]-benzoxazole (BF-168), that demonstrated abundant initial brain uptake (3.9% injected dose/gm at 2 min after injection) and fast clearance ($t_{1/2}$=24.7 min) after intravenous (iv) administration in normal mice. In addition, autoradiograms of brain sections from APP23 transgenic mice at 180 min after iv injection of $^{18}$F-radiolabeled BF-168 showed selective labeling of brain amyloid deposits with little non-specific binding.

More recently, Kudo et al. (in *J. Nucl. Med.* 2007, 48553) have demonstrated the use of a novel compound, F-18 labeled 2-(2-[2-diethylaminothiazol-5-yl]-ethenyl)-6-(2-[fluoro]) ethoxybenzoxazol (eB F-227) as a promising PET probe for in vivo detection of dense amyloid deposits in AD patients.

U.S. Pat. Nos. 6,001,331 and 6,696,039 B2, issued Dec. 14, 1999 and Feb. 24, 2004, respectively, hereby incorporated by reference, describe the use of several radiolabeled benzothiazole compounds for imaging amyloid deposits.

U.S. Pat. Nos. 6,168,776 and 6,133,259, issued Jan. 2, 2001 and Oct. 17, 2000, respectively, hereby incorporated by reference describe amyloid-binding compounds such as Chrysamine G and their use in identifying AD in vivo and other pathological conditions characterized by amyloidosis.

One promising amyloid imaging agent is an analogue of thioflavin T, also known as the Pittsburgh Compound-B or "PIB compound." PIB is also known as [N-methyl-($^{11}$C)]-2-(4'-methylaminophenyl)-6-hydroxybenzothiazole (or [$^{11}$C] 6-OH-BTA-I). PET imaging with $^{11}$C-PIB can discriminate AD from frontotemporal lobar degeneration (FTLD). See *J. Med. Chem.* 2003, 46(13), 2740; PCT Application No. PCT/US2005/023618; U.S. Pat. Nos. 6,114,175, 6,113,259, 6,168, 776, 6,417,178, 7,270,800, 7,351,401; U.S. Patent Application No. 2008/00210777; and *Neurology* 2007, 68, 1205. However, use of a C-11 labeled tracer limits imaging to medical centers with a cyclotron.

Accordingly, there is a need to provide compounds and methods for imaging and treating AD and amyloidosis-associated pathological conditions that are easily available and cost effective. There is a continuing need to seek novel amyloid imaging tracers that are accurate and used in early detection of AD and other pathological conditions associated with amyloidosis.

SUMMARY

One aspect of the present invention relates to compounds, compositions and methods for diagnosis and/or treatment of a subject suffering from an amyloidosis-associated pathological condition. In certain embodiments, the imaging and/or therapeutic agents of the instant invention may be administered to a subject for identification and/or treatment of amyloid deposits.

One aspect of the invention relates to radiolabeled 2-(4'-methylamino)phenyl)-6-hydroxybenzothiazoles, and derivatives thereof, and compositions and methods of use thereof. For example, in certain embodiments, the invention relates to [N-2[18F]fluoropropyl]-2-(4'-(methylamino)phenyl)-6-hydroxybenzothiazole (F-18MHT). In certain embodiments, the invention relates to compositions which comprise a diagnostic radioimaging amount of F-18MHT, in combination with a pharmaceutical carrier in an appropriate dosage. It is disclosed herein that F-18MHT exhibits abundant initial brain uptake of 4% injected dose (ID) per gram at the first 2 min and 1.2% ID per gram at 45 min. In addition, it is shown that F-18MHT can be used in conjunction with mannitol to increase brain uptake of the radiolabel.

Another aspect of the invention relates to radiolabeled dimers of 2-(4'-methylamino)phenyl)-6-hydroxybenzothiazoles, and derivatives thereof, and compositions and methods of use thereof For example, in certain embodiments, the invention relates to a dimer of [N-2[18F]fluoropropyl]-2-(4'-(methylamino)phenyl)-6-hydroxybenzothiazole (F-18MHT). In certain embodiments, the invention relates to compositions which comprise a diagnostic radioimaging amount of a dimer of F-18MHT, in combination with a pharmaceutical carrier in an appropriate dosage.

The imaging agents of the instant invention may be administered to the subject for identification of amyloid deposits. A specific imaging method detects amyloid deposits by administering the imaging agent to the subject and detecting the spatial distribution of the agent. Differential accumulation of the agent is indicative of AD or an amyloidosis-associated pathological condition and can be monitored by using a PET or SPECT camera.

Other features, objects, and advantages of the present invention are apparent in the detailed description that follows. It should be understood, however, that the detailed description is given by way of illustration only, not limitation. Various changes and modifications within the scope of the invention will become apparent to those skilled in the art from the detailed description.

BRIEF DESCRIPTION OF THE FIGURES

FIG. 5 depicts a table showing the some of the effects of amyloid buildup.

DETAILED DESCRIPTION

Figure 1:
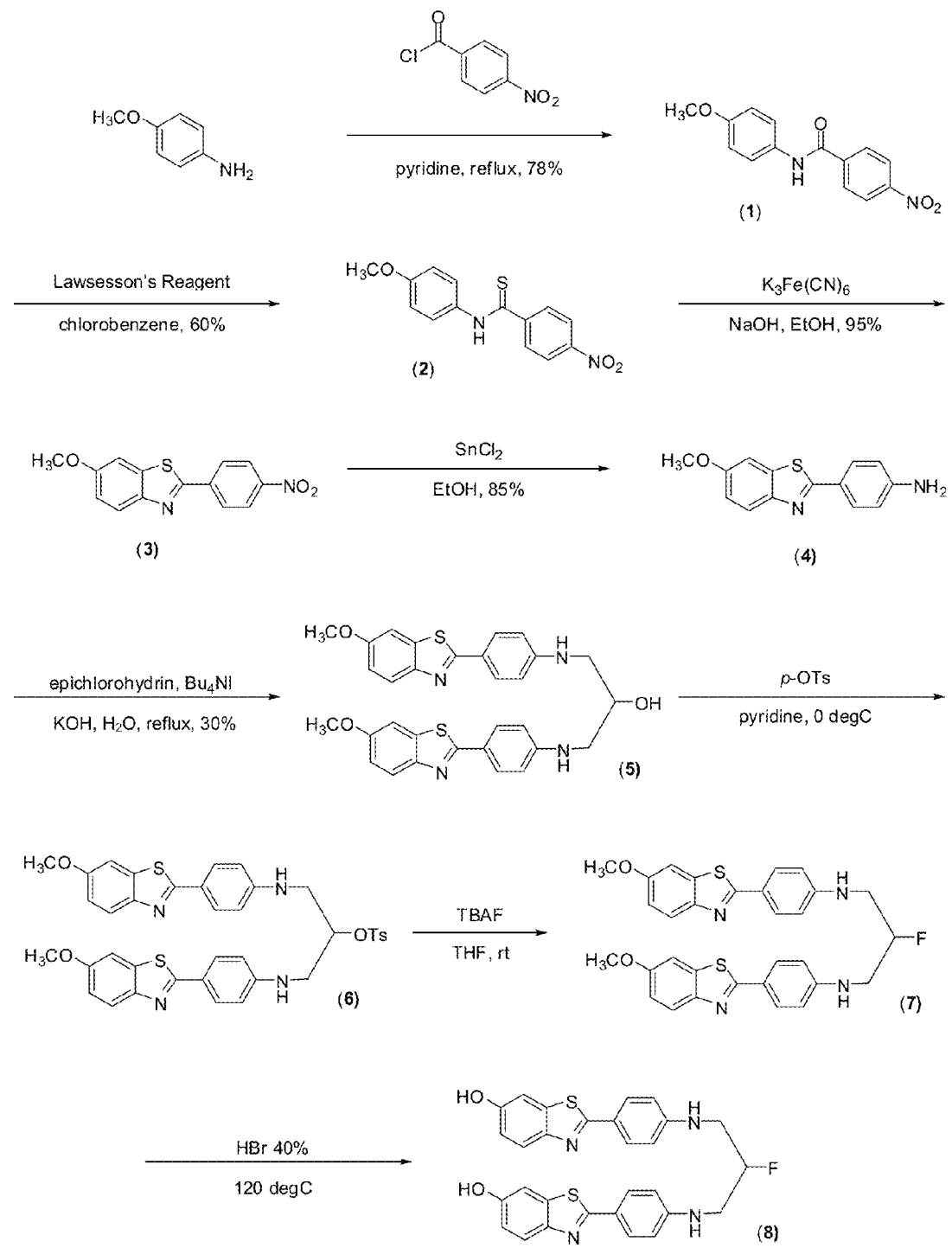
FIG. 1 depicts one approach to the synthesis of a dimer of F-18MHT (8).

One aspect of the present invention provides embodiments of compounds, compositions and methods for effective administration to a subject suffering from amylodiosis-associated pathological conditions, such as Alzheimer's disease (AD). In certain embodiments of the invention, the compounds are reversible choline esterase inhibitors that show high brain uptake. In certain embodiment, the compounds inhibit β-(A β-) protein folding that causes amyloid plaque formation. Further, in certain embodiments, the compounds are labeled with a PET or SPECT radionuclide, and can be used for diagnosing amyloid deposits in patients suffering from Alzheimer's disease and/or pathological conditions characterized by the presence of amyloid deposits. In certain embodiments, the novel imaging compounds act on both potential Alzheimer disease progressions.

One aspect of the invention relates to the preparation of fluorinated or radiofluorinated 2-(4'-methylamino)phenyl)-6-hydroxybenzothiazoles, and their diagnostic and/or therapeutic use in amylodiosis-associated pathological conditions. For example in brain disorders associated with aging, such as, senile dementia and Alzheimer's disease. In certain embodiments, the compositions comprise an effective amount of a fluorinated 2-(4'-methylamino)phenyl)-6-hydroxybenzothiazole, in combination with a pharmaceutical carrier in an appropriate dosage. In certain embodiments, the compositions comprise a diagnostic radioimaging amount of a $^{18}$F-labeled fluorinated 2-(4'-methylamino)phenyl)-6-hydroxybenzothiazole, in combination with a pharmaceutical carrier in an appropriate dosage. In certain embodiments, the comositions further comprise a sugar alcohol (e.g. mannitol).

Another aspect of the invention relates to the preparation of fluorinated or radiofluorinated dimers of 2-(4'-methylamino)phenyl)-6-hydroxybenzothiazoles, and their diagnostic and/or therapeutic use in amylodiosis-associated pathological conditions. For example in brain disorders associated with aging, such as, senile dementia and Alzheimer's disease. In certain embodiments, the compositions comprise an effective amount of a fluorinated dimer of a 2-(4'-methylamino)phenyl)-6-hydroxybenzothiazole, in combination with a pharmaceutical carrier in an appropriate dosage. In certain embodiments, the compositions comprise a diagnostic radioimaging amount of a $^{18}$F-labeled fluorinated dimer of a 2-(4'-methylamino)phenyl)-6-hydroxybenzothiazole, in combination with a pharmaceutical carrier in an appropriate dosage. In certain embodiments, the comositions further comprise a sugar alcohol (e.g. mannitol).

In certain embodiments, imaging and/or therapeutic agents of the instant invention may be administered to a subject for identification of amyloid deposits. A specific imaging method detects amyloid deposits by administering the imaging agent to the subject and detecting the spatial distribution of the agent. Differential accumulation of the agent is indicative of AD or an amyloidosis-associated pathological condition and can be monitored by using a PET or SPECT camera.

Amyloidosis is a condition characterized by the accumulation of various insoluble, fibrillar proteins in the tissues of a patient. An amyloid deposit is formed by the aggregation of amyloid proteins, followed by the further combination of aggregates and/or amyloid proteins.

Many forms of amyloidosis exist, and the disease can be classified into four groups: primary amyloidosis, secondary amyloidosis, hereditary amyloidosis, and amyloidosis associated with normal aging. Primary amyloidosis (light chain amyloidosis) occurs with abnormalities of plasma cells, and some people with primary amyloidosis also have multiple myeloma (cancer of the plasma cells). Typical sites of amyloid buildup in primary amyloidosis are the heart, lungs, skin, tongue, thyroid gland, intestines, liver, kidneys, and blood vessels. Secondary amyloidosis may develop in response to various diseases that cause persistent infection or inflammation, such as tuberculosis, rheumatoid arthritis, and familial Mediterranean fever. Typical sites of amyloid buildup in secondary amyloidosis are the spleen, liver, kidneys, adrenal glands, and lymph nodes. Hereditary amyloidosis has been noted in some families, particularly those from Portugal, Sweden, and Japan. The amyloid-producing defect occurs because of mutations in specific proteins in the blood. Typical sites for amyloid buildup in hereditary amyloidosis are the nerves, heart, blood vessels, and kidneys. See FIG. 5 for a table showing the some of the effects of amyloid buildup.

In certain embodiments, the present invention is directed to a method of identifying a patient as prodromal to a standard clinical diagnosis of a amyloid deposition disease. The method involves the use of amyloid imaging agents to obtain quantitative and qualitative data from a patient. Quantitative and qualitative amyloid imaging, in accordance with the present invention, should allow for earlier and more accurate diagnosis of amyloid deposit diseases, and should aid in the development of anti-amyloid therapies. In certain embodiments, the target patient for this methodology is a patient presenting signs of clinical dementia or a patient exhibiting clinical signs of mild cognitive impairment.

The category of diseases associated with amyloid deposition (i.e. "amylodiosis-associated pathological conditions") includes but is not limited to Alzheimer's Disease, idiopathetic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Kum, medullary carcinoma of the thyroid, isolated atrial amyloid, $\beta_2$-microglobulin amyloid in dialysis patients, inclusion body myositis, $\beta_2$-amyloid deposits in muscle wasting disease, and Islets of Langerhans diabetes Type I1 insulinoma. Type 2 diabetes mellitus, hereditary cerebral hemorrhage amyloidosis (Dutch), amyloid A (reactive), secondary amyloidosis, familial Mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish)), familial amyloid cardiomyopathy (Danish), isolated cardiac amyloid, systemic senile amyloidoses, AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-I (familial amyloidotic polyneuropathy-Iowa), AApo-A-II (accelerated senescence in mice), fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele, and the condition associated with homozygosity for the apolipoprotein E4 allele or Huntingdon's disease. In certain embodiments, the disease associated with amyloid deposition is a amyloid plaque deposition disease. In certain embodiments, the disease associated with amyloid deposition is AD.

One aspect of the invention relates to a basic methodology of identifying a patient as prodromal to an amyloid deposition disease entails: administering to the patient, who is presenting with signs of clinical dementia or presenting with clinical signs of a mild cognitive impairment, in need thereof an effective amount of compound of the invention as described herein (e.g. a compound of formula I-IV); imaging said patient to obtain data; and analyzing said data to ascertain amyloid levels in said patient with reference to a normative patient.

One skilled in the art would recognize that the practitioner may apply different criteria for a determination of signs of clinical dementia. Such criteria include, but are not limited to Diagnostic and Statistical Manual of Mental Disorders, third edition (DSM-III) Alzheimer's Disease Diagnostic and Treatment Center (ADDTC), International Statistical Classification of Diseases, 10* Revision (ICD-IO), National Institute of Neurological Disorders and Stroke-Association Internationale pour Ia Recherche et PEnseignment en Neurosciences (NINDS-AIREN) and Diagnostic and Statistical Manual of Mental Disorders, Fourth Edition (DSM-IV). See Pohjasvaara et al, *Stroke* 2000, 31, 2952-2957. Clinical characterization of a patient as mild cognitive impairment is well within the skill of the practitioner. Such testing of a patient to elucidate such a condition involves performing a series of mental tests. The methods for clinical diagnosis are widely reviewed and are discussed in, e.g., Petersen et al., *Arch. Neurol.* 1999, 56, 303-308. Based on clinical testing alone, subjects identified with MCI may convert to a diagnosis of AD (at a rate of about 10-15% per year), remain MCI, or revert to a diagnosis of "normal" (10-15% per year). See Larrieu, S et al., *Neurology* 1926, 59, 1594-1599. Therefore, there is considerable prognostic uncertainty associated with this clinical diagnosis. The ability to identify the presence or absence of brain amyloid deposition in a subject clinically diagnosed with MCI has the potential to greatly increase the accuracy of prognosis for conversion to AD.

One embodiment of the invention relates to a method for diagnosing a patient presenting with a dementing disorder of questionable etiology. This method would involve determining if dementias of questionable etiology are likely to be AD or another amyloid deposition disorder based on the finding of amyloid deposition. This method would involve administering to a patient a compound of the invention as described herein; imaging the patient to obtain data; and determining if the dementia of questionable etiology is AD based on the finding of amyloid deposition.

Another embodiment of the invention is a method of manufacturing a medicament for identifying a patient as prodromal to an amyloid deposition disease as described in any of the foregoing or following embodiments. The method comprises combining a compound of the invention as described herein, with a pharmaceutical carrier to form the medicament.

Yet another embodiment is a method of manufacturing a medicament for diagnosing a patient presenting with a dementing disorder of questionable etiology as set forth in any of the foregoing or following embodiments. The method comprises combining a compound of the invention as described herein, with a pharmaceutical carrier to form the medicament. As used herein, the term "dementing disorder of questionable etiology" refers to the condition in which a person presents for clinical evaluation (which may consist of neurological, psychiatric, medical and neuropsychological evaluations commonly employed by those skilled in the art of diagnosing persons with dementing disorders) and, after that clinical evaluation, the evaluator finds evidence that some dementing disorder may be present (based on evidence of subjective memory complaints, description of memory complaints by informants familiar with the persons deviation from normal functioning, or poor performance on neuropsychological and clinical tests commonly used by those skilled in the art), but, can not find sufficient evidence for any single clinically defined dementing disorder (such as AD, frontotemporal dementia, Dementia with Lewy Bodies, Vascular dementia, pseudodementia due to Major Depression, Creutzfeld Jacob disease and others known to those skilled in the art) or finds that the person shows evidence of more than one single dementing disorder to the degree that the distinction between these two (or more) dementing disorders is questionable in this person.

Certain aspects of the invention relate to compounds of the invention which are amyloid imaging agents which, in conjunction with non-invasive neuroimaging techniques such as magnetic resonance spectroscopy (MRS) or imaging (MRI), or gamma imaging such as positron emission tomography (PET) or single-photon emission computed tomography (SPECT), are used to quantify amyloid deposition in vivo. These imaging techniques acquire data on many brain regions. Quantitation on specific regions is achieved by delineating "regions of interest or ROI".

Pursuant to the invention, data obtained from patients using one of the imaging techniques mentioned above can be compared to data from normative patients with a conclusion based on criteria which distinguish the patient as prodromal to a standard clinical diagnosis of an amyloid deposition disease.

Using the same protocol, one can compare data obtained from the imaging techniques applied to the patients in order to: define a dementing disorder of questionable etiology as being caused by an amyloid deposition disease; distinguish Alzheimer's disease from frontotemporal dementia; monitor a patient to determine onset of Alzheimer's disease; diagnose Alzheimer's disease in a patient clinically diagnosed with mild cognitive impairment; identify a patient as prodromal to Alzheimer's disease; identify a patient as having a disease associated with an amyloid deposition disorder wherein the patient is presenting with a dementing disorder of questionable etiology or identify a patient as having Alzheimer's disease wherein the patient is presenting with a dementing disorder of questionable etiology.

Radioimaging methods that may be employed in accordance with the present inventions are known in the art. See U.S. Pat. No. 6,187,286 and U.S. Patent Publication No. 2006/0140859; both of which are hereby incorporated by reference.

In accordance with the invention, the targeting molecule is in association with (spatial proximity to) the radionuclide. Spatial proximity between the targeting molecule and the radionuclide may be effected in any manner which preserves the specificity of the targeting molecule for its target tissue. For example, spatial proximity between the radionuclide and the targeting molecule may be effected by a covalent or non-covalent chemical bond. Such a chemical bond may be effected through a chelating substance and/or an auxiliary molecule such as mannitol, gluconate, glucoheptonate, tartrate, and the like.

Alternatively, spatial proximity between the nuclide and the targeting molecule may be effected by incorporating the radionuclide and the targeting molecule in a micelle or liposome, in such a way that the affinity of the targeting molecule for its target tissue is maintained. Spatial proximity between the radionuclide and the targeting molecule may also be effected by attaching the radionuclide and the targeting molecule to a matrix such, as a microsphere or liposomes.

A radionuclide may be incorporated into the imaging agent by covalent bonding directly to an atom of the targeting molecule, or the radionuclide may be noncovalently or covalently associated with the targeting molecule through a chelating structure or through an auxiliary molecule such as mannitol, gluconate, glucoheptonate, tartrate, and the like. When a chelating structure is used to provide spatial proximity between the radionuclide and the targeting molecule, the chelating structure may be directly associated with the targeting molecule or it may be associated with the targeting molecule through an auxiliary molecule such as mannitol, gluconate, glucoheptonate, tartrate, and the like.

Any suitable chelating structure may be used to provide spatial proximity between the radionuclide and the targeting molecule of the agent through covalent or noncovalent association. Many such chelating structures are known in the art. Preferably, the chelating structure is an $N_2S_2$ structure, an $NS_3$ structure, an $N_4$ structure, an isonitrile containing structure, a hydrazine containing structure, a HYNIC (hydrazinonicotinic acid) group-containing structure, a 2-methylthiolnicotinic acid group-containing structure, a carboxylate group containing structure, and the like. In some cases, chelation can be achieved without including a separate chelating structure, because the radionuclide chelates directly to atom(s) in the targeting moiety, for example to oxygen atoms in the phosphate group(s) or in carboxylate group(s).

The chelating structure, auxiliary molecule, or radionuclide may be placed in spatial proximity to any position of the targeting molecule which does not interfere with the interaction of the targeting molecule with its receptor in tumors. The chelating structure, auxiliary molecule, or radionuclide may be covalently or non-covalently associated with any moiety of the targeting molecule except the receptor-binding moiety.

After the labeling reaction is complete, the reaction mixture may optionally be purified using one or more high performance liquid chromatography (HPLC) steps. Any suitable HPLC system may be used if a purification step is performed, and the yield of imaging agent obtained from the HPLC step may be optimized by varying the parameters of the HPLC system, as is known in the art. Any HPLC parameter may be varied to optimize the yield of the imaging agent of the invention. For example, the pH may be varied, e.g., raised, to decrease the elution time of the peak corresponding to the imaging agent of the invention.

The invention as embodied in a kit for radioimaging comprises a radioimaging agent described above, in combination with a pharmaceutically acceptable carrier such as human serum albumin. Human serum albumin for use in the kit of the invention may be made in any way, for example, through purification of the protein from human serum or though recombinant expression of a vector containing a gene encoding human serum albumin. Other substances may also be used as carriers in accordance with this embodiment of the invention, for example, detergents, dilute alcohols, carbohydrates, auxiliary molecules, and the like. The kit of the invention may of course also contain such other items as may facilitate its use, such as syringes, instructions, reaction vials, and the like.

In one embodiment, a kit according to the invention contains from about 1 to about 30 mCi of the radionuclide-labeled amyloid imaging agent described herein, in combination with a pharmaceutically-acceptable carrier. The amyloid imaging agent and carrier may be provided in solution or in lyophilized form. When the amyloid imaging agent and carrier of the kit are in lyophilized form, the kit may optionally contain a sterile and physiologically acceptable reconstitution medium such as water, saline, buffered saline, and the like.

The radioimaging agents of the invention may be used in accordance with the methods of the invention by those of skill in the art, e.g., by specialists in nuclear medicine, to image tissue in a mammal. Any mammalian tumor may be imaged the imaging agents of the invention. Images are generated by virtue of differences in the spatial distribution of the imaging agents which accumulate in the various tissues and organs of the mammal. The spatial distribution of the imaging agent accumulated in a mammal, in an organ, or in a tissue may be measured using any suitable means, for example, a PET or single photon emission computer tomography (SPECT) imaging camera apparatus, and the like.

PET imaging is accomplished with the aid of tracer compounds labeled with a positron-emitting isotope (Goodman, M. M. Clinical Positron Emission Tomography, Mosby Yearbook, 1992, K. F. Hubner et al., Chapter 14). These tracer compounds can be labeled with a positron-emitting radionuclide that includes $^{18}F$ and $^{76}Br$. In general, a PET label, is a label which is covalently attached to the remainder of a molecule and should have a half life of at least about 5-20 minutes, preferably about 60 minutes or more. Examples of PET labels include $^{18}F$, $^{13}N$, $^{76}Br$ (half life=16.1 hrs), $^{77}Br$, $^{15}O$, $^{68}Ga$ (half life=68.3 min), $^{62}Cu$ (half life=9.74 min), $^{64}Cu$ (half life=12.7 hrs), $^{82}Rb$ (half life=78 sec), and $^{24}I$ (half life=4.18 days)

The use of $^{18}F$-labeled compounds in PET has thus far been limited to a few analog compounds. Most notably, 18-fluorodeoxyglucose has been widely used in studies of glucose metabolism and localization of glucose uptake associated with brain activity. More recently, other analogs, such as $^{18}$F-methyl choline (for prostate cancers; see *Cancer Res.* 2001, 6, 110), $^{18}$F-fluorothymidine (for lung tumors; see *J. Nucl. Med.* 2003, 44, 1426; and *Eur. J. Nuc. Mol. Imaging* 2003, 30, 1407) and O-(2-[$^{18}$F]fluoroethyl)-L-tyrosine (U.S. Pat. No. 7,138,540; hereby incorporated by reference), have also been employed in PET imaging. For examples of $^{18}$F-labeling imaging agents see: *Eur. J. Med. Chem.* 1994, 29, 115; *Eur. J. Med. Chem.* 1994, 29, 955; *J. Heterocyclic Chem.* 1993, 30, 1337; *Organic Process Research & Development* 2005, 9(6), 774; *J. Med. Chem.* 2005, 48(16), 5290; *J. Med. Chem.* 1990, 33, 1482; *Nuclear Medicine and Biology* 2001, 28(6), 683; *and Nuclear Medicine and Biology* 2004, 31(4), 483.

For SPECT imaging, the inventive compound can be labeled with a γ-emitting nuclide, such as, for example, $^{99m}$Tc, $^{111}$In, $^{67}$Ga, $^{201}$Tl, $^{123}$I, $^{133}$Xe and others.

For fluorescence tomography imaging, the inventive compound can be conjugated to a near infra red moiety, such as CY5 (Cyanine dye). Fluorescence tomography is under development.

The imaging agents of the instant invention are used in the following manner. An effective amount of an imaging agent comprising at least one targeting molecule and a nuclide (from 1 to 50 mCi) may be combined with a pharmaceutically-acceptable carrier for use in imaging studies. In accordance with the invention, "an effective amount" of the imaging agent of the invention is defined as an amount sufficient to yield an acceptable image using equipment which is available for clinical use. An effective amount of the imaging agent of the invention may be administered in more than one injection. Effective amounts of the imaging agent of the invention will vary according to factors such as the degree of susceptibility of the individual, the age, sex, and weight of the individual, idiosyncratic responses of the individual, and the dosimetry. Effective amounts of the imaging agent of the invention will also vary according to instrument and film-related factors. Optimization of such factors is well within the level of skill in the art.

The data obtained in any method described herein can be quantitatively expressed in terms of Standardized Uptake Value (SUV) or in terms of pharmacokinetic modeling parameters such as the Logan distribution volume ratio (DVR) to a reference tissue such as cerebellum. Subjects who are more than one standard deviation above the typical control value of SUV or DVR would be considered to have a "positive" test and be considered to be prodromal to a clinical diagnosis of an amyloid deposition disease such as AD. Specifically, subjects will be considered "positive" if their 40-60 min average SUV is greater than 1.0 in frontal, parietal or posterior cingulate cortex. This value clearly separated AD patients from controls in the initial human study. See Klunk, W. E. et al., *Ann. Neurol.* 2004, 55(3), 306-19. Likewise, subjects can be considered "positive" if their Logan DVR value exceeds 1.5 in frontal, parietal or posterior cingulate cortex. These brain areas and exact cutoffs are given only as examples and further work may disclose additional brain areas that are useful and the cutoff values may be refined and other modeling techniques (such as compartmental modeling, graphical analysis, reference tissue modeling or spectral analysis) may be applied to determine the cutoffs. In addition, the scan data can be qualitatively interpreted from images that reflect the regional brain distribution of either SUV, Logan DVR or other parameters in which one having ordinary skill in the art of interpreting PET scans can determine that the qualitative amount and distribution of amyloid is consistent with a prodromal phase of a clinically diagnosed amyloid deposition disease.

Selected Compounds of the Invention

One aspect of the invention relates to a compound of formula I, II, III, or IV, or a pharmaceutically acceptable salt thereof:

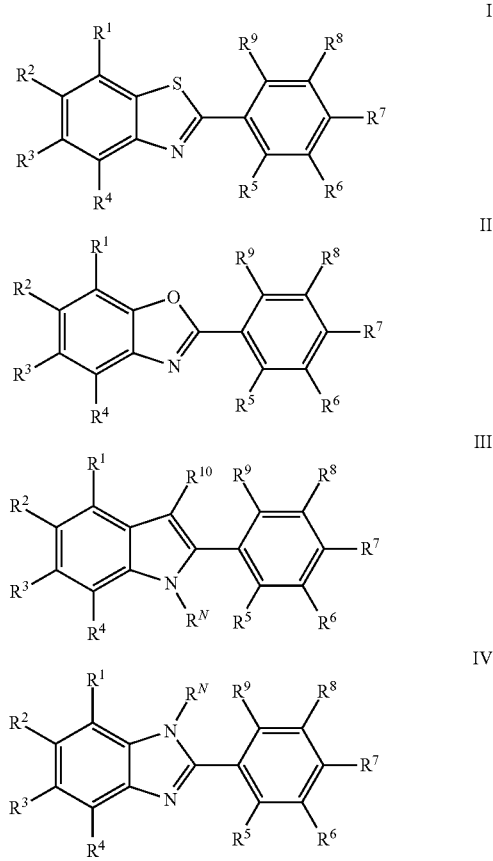

wherein, independently for each occurrence, $R^1$, $R^2$, $R^3$, $R^4$, $R^5$, $R^6$, $R^7$, $R^8$, $R^9$, and $R^{10}$ are hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —Y-(haloalkylene)-alkyl;

$R^N$ is hydrogen, lower alkyl, or -(haloalkylene)-alkyl;

Y is a bond, N($R^N$), O, or S;

provided that at least one of $R^1$, $R^2$, $R^3$, $R^4$, $R^5$, $R^6$, $R^7$, $R^8$, $R^9$, or $R^{10}$ is —Y-(haloalkylene)-alkyl; or $R^N$ is -(haloalkylene)-alkyl.

Such compounds (i.e. those containing secondary and/or tertiary halogens) should be more stabile under biological conditions, as compared to related compounds containing primary halogens.

In certain embodiments, the present invention relates to compounds represented by formula I and any of the attendant definitions.

In certain embodiments, the present invention relates to compounds represented by formula II and any of the attendant definitions.

In certain embodiments, the present invention relates to compounds represented by formula III and any of the attendant definitions.

In certain embodiments, the present invention relates to compounds represented by formula IV and any of the attendant definitions.

In certain embodiments, the present invention relates to compounds represented by formula I-IV and any of the attendant definitions, wherein $R^7$ is —Y-(haloalkylene)-alkyl.

In certain embodiments, the present invention relates to compounds represented by formula I-IV and any of the attendant definitions, wherein $R^7$ is —Y-(fluoroalkylene)-alkyl.

In certain embodiments, the present invention relates to compounds represented by formula I-IV and any of the attendant definitions, wherein $R^7$ is —Y-(monofluoroalkylene)-alkyl.

In certain embodiments, the present invention relates to compounds represented by formula I-IV and any of the attendant definitions, wherein $R^7$ is —Y-(monofluoroalkylene)-alkyl; and said fluoro substituent is bound to a secondary alkylene carbon.

In certain embodiments, the present invention relates to compounds represented by formula I-IV and any of the attendant definitions, wherein $R^7$ is —Y-(monofluoroalkylene)-alkyl; and said fluoro substituent is bound to a tertiary alkylene carbon.

In certain embodiments, the present invention relates to compounds represented by formula I-IV and any of the attendant definitions, wherein $R^7$ is —Y—([F-18]fluoroalkylene)-alkyl.

In certain embodiments, the present invention relates to compounds represented by formula I-IV and any of the attendant definitions, wherein $R^7$ is —Y—([F-18]monofluoroalkylene)-alkyl; and said [F-18]fluoro substituent is bound to a secondary alkylene carbon.

In certain embodiments, the present invention relates to compounds represented by formula I-IV and any of the attendant definitions, wherein $R^7$ is —Y—([F-18]monofluoroalkylene)-alkyl; and said [F-18]fluoro substituent is bound to a tertiary alkylene carbon.

In certain embodiments, the present invention relates to compounds represented by formula I-IV and any of the attendant definitions, wherein $R^7$ is —Y—(CH$_2$CH$^{18}$F)—CH$_3$.

In certain embodiments, the present invention relates to compounds represented by formula I-IV and any of the attendant definitions, wherein Y is N($R^N$).

In certain embodiments, the present invention relates to compounds represented by formula I-IV and any of the attendant definitions, wherein $R^N$ is hydrogen.

In certain embodiments, the present invention relates to compounds represented by formula I-IV and any of the attendant definitions, wherein $R^1$, $R^3$, $R^4$, $R^5$, $R^6$, $R^8$, and $R^9$ are hydrogen.

In certain embodiments, the present invention relates to compounds represented by formula I-IV and any of the attendant definitions, wherein $R^2$ is hydroxy, alkoxy, aryloxy, heteroaryloxy, aralkyloxy, or heteroaralkyloxy.

In certain embodiments, the present invention relates to compounds represented by formula I-IV and any of the attendant definitions, wherein $R^2$ is hydroxy.

In certain embodiments, the present invention relates to compounds represented by formula I-IV and any of the attendant definitions, wherein $R^{10}$ is hydrogen.

In certain embodiments, the present invention relates to compounds represented by formula I and any of the attendant definitions, wherein $R^7$ is —N(H)-(monofluoroalkylene)-CH$_3$; $R^1$, $R^3$, $R^4$, $R^5$, $R^6$, $R^8$ and $R^9$ are hydrogen; and $R^2$ is hydroxy.

In certain embodiments, the present invention relates to compounds represented by formula I and any of the attendant definitions, wherein $R^7$ is —N(H)—([F-18]monofluoroalkylene)-CH$_3$; $R^1$, $R^3$, $R^4$, $R^5$, $R^6$, $R^8$, and $R^9$ are hydrogen; and $R^2$ is hydroxy.

In certain embodiments, the present invention relates to compounds represented by formula I and any of the attendant definitions, wherein $R^7$ is —N(H)—(CH$_2$CHF)—CH$_3$; $R^1$, $R^3$, $R^4$, $R^5$, $R^6$, $R^7$, and $R^8$ are hydrogen; and $R^2$ is hydroxy.

In certain embodiments, the present invention relates to compounds represented by formula I and any of the attendant definitions, wherein $R^7$ is —N(H)—(CH$_2$CH$^{18}$F)—CH$_3$; $R^1$, $R^3$, $R^4$, $R^5$, $R^6$, $R^8$, and $R^9$ are hydrogen; and $R^2$ is hydroxy.

In certain embodiments, the present invention relates to compounds represented by formula I and any of the attendant definitions, wherein the compound is

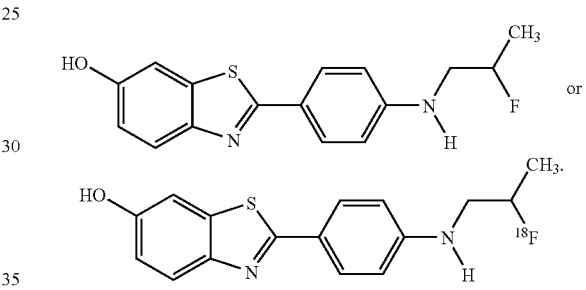

Another aspect of the invention relates to a compound of formula I, II, III, or IV, or a pharmaceutically acceptable salt thereof:

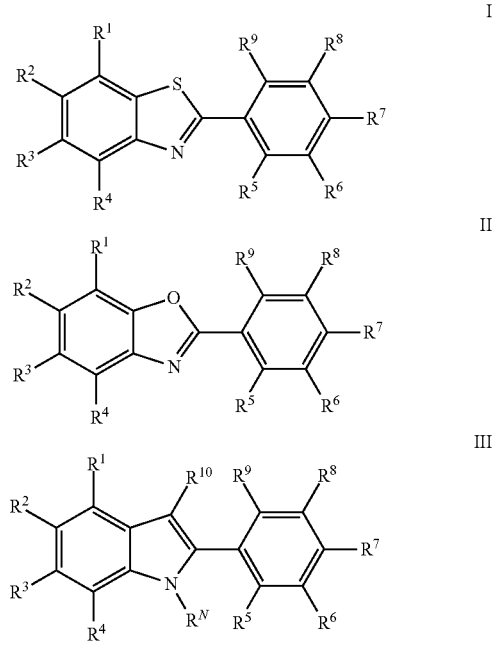

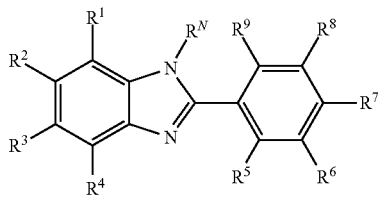

wherein, independently for each occurrence, $R^1$, $R^2$, $R^3$, $R^4$, $R^5$, $R^6$, $R^8$, $R^9$, and $R^{10}$ are hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, or isocyano;

$R^7$ is —Y-(haloalkylene)-R;

Y is a bond, N($R^N$), O, or S;

$R^N$ is hydrogen, or lower alkyl; and

R is

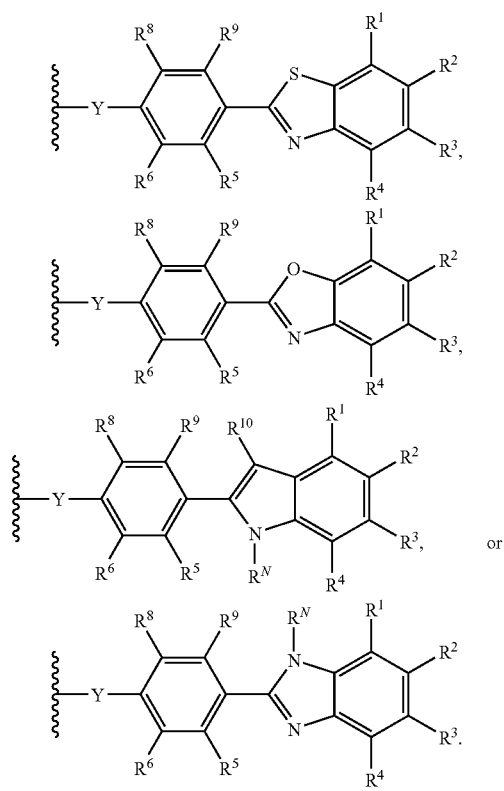

In certain embodiments, the present invention relates to compounds represented by formula I and any of the attendant definitions.

In certain embodiments, the present invention relates to compounds represented by formula II and any of the attendant definitions.

In certain embodiments, the present invention relates to compounds represented by formula III and any of the attendant definitions.

In certain embodiments, the present invention relates to compounds represented by formula IV and any of the attendant definitions.

In certain embodiments, the present invention relates to compounds represented by formula I-IV and any of the attendant definitions, wherein $R^7$ is —Y-(haloalkylene)-Y—R.

In certain embodiments, the present invention relates to compounds represented by formula I-IV and any of the attendant definitions, wherein $R^7$ is —Y-(fluoroalkylene)-Y—R.

In certain embodiments, the present invention relates to compounds represented by formula I-IV and any of the attendant definitions, wherein $R^7$ is —Y-(monofluoroalkylene)-Y—R.

In certain embodiments, the present invention relates to compounds represented by formula I-IV and any of the attendant definitions, wherein $R^7$ is —Y—([F-18]fluoroalkylene)-Y—R.

In certain embodiments, the present invention relates to compounds represented by formula I-IV and any of the attendant definitions, wherein $R^7$ is —Y—([F-18]monofluoroalkylene)-Y—R.

In certain embodiments, the present invention relates to compounds represented by formula I-IV and any of the attendant definitions, wherein Y is N($R^N$).

In certain embodiments, the present invention relates to compounds represented by formula I-IV and any of the attendant definitions, wherein $R^N$ is hydrogen.

In certain embodiments, the present invention relates to compounds represented by formula I-IV and any of the attendant definitions, wherein $R^7$ is —N(H)-(haloalkylene)-N(H)—R.

In certain embodiments, the present invention relates to compounds represented by formula I-IV and any of the attendant definitions, wherein $R^1$, $R^3$, $R^4$, $R^5$, $R^6$, $R^8$, and $R^9$ are hydrogen.

In certain embodiments, the present invention relates to compounds represented by formula I-IV and any of the attendant definitions, wherein $R^2$ is hydroxy, alkoxy, aryloxy, heteroaryloxy, aralkyloxy, or heteroaralkyloxy.

In certain embodiments, the present invention relates to compounds represented by formula I-IV and any of the attendant definitions, wherein $R^2$ is hydroxy.

In certain embodiments, the present invention relates to compounds represented by formula I-IV and any of the attendant definitions, wherein $R^{10}$ is hydrogen.

In certain embodiments, the present invention relates to compounds represented by formula I and any of the attendant definitions, wherein $R^7$ is —Y-(haloalkylene)-Y—R; and R is

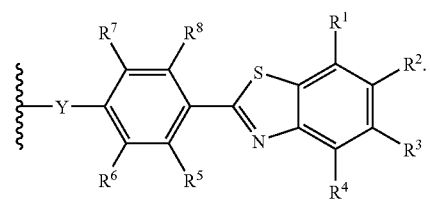

In certain embodiments, the present invention relates to compounds represented by formula II and any of the attendant definitions, wherein $R^7$ is —Y-(haloalkylene)-Y—R; and R is

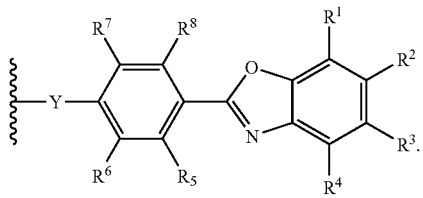

In certain embodiments, the present invention relates to compounds represented by formula III and any of the attendant definitions, wherein $R^7$ is —Y-(haloalkylene)-Y—R; and R is

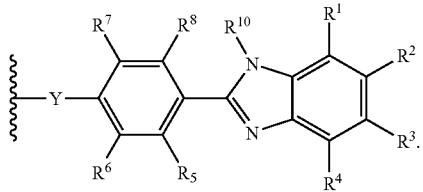

In certain embodiments, the present invention relates to compounds represented by formula IV and any of the attendant definitions, wherein $R^7$ is —Y-(haloalkylene)-Y—R; and R is

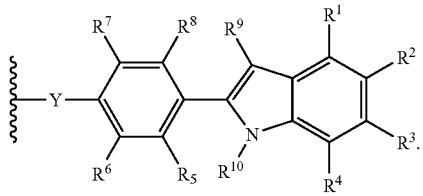

In certain embodiments, the present invention relates to compounds represented by formula I and any of the attendant definitions, wherein $R^7$ is —N(H)-(monofluoroalkylene)-N(H)—R; R is

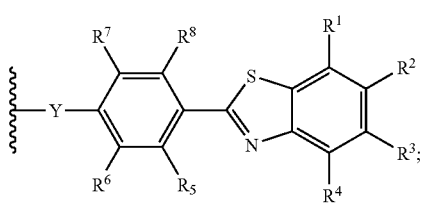

$R^1$, $R^3$, $R^4$, $R^5$, $R^6$, $R^8$, and $R^9$ are hydrogen; and $R^2$ is hydroxy.

In certain embodiments, the present invention relates to compounds represented by formula I and any of the attendant definitions, wherein $R^7$ is —N(H)—([F-18]monofluoroalkylene)-N(H)—R; R is

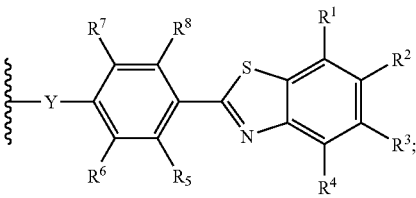

$R^1$, $R^3$, $R^4$, $R^5$, $R^6$, $R^8$, and $R^9$ are hydrogen; and $R^2$ is hydroxy.

In certain embodiments, the present invention relates to compounds represented by formula I and any of the attendant definitions, wherein $R^7$ is —N(H)—(CH$_2$CHFCH$_2$)—N(H)—R; R is

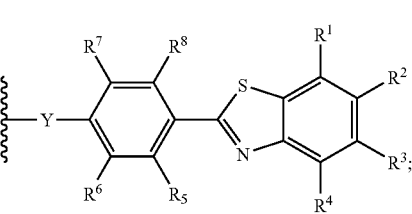

$R^1$, $R^3$, $R^4$, $R^5$, $R^6$, $R^8$, and $R^9$ are hydrogen; and $R^2$ is hydroxy.

In certain embodiments, the present invention relates to compounds represented by formula I and any of the attendant definitions, wherein $R^7$ is —N(H)—(CH$_2$CH$^{18}$FCH$_2$)—N(H)—R; R is

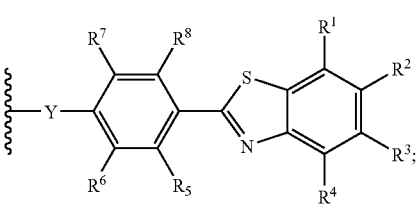

$R^1$, $R^3$, $R^4$, $R^5$, $R^6$, $R^8$, and $R^9$ are hydrogen; and $R^2$ is hydroxy.

In certain embodiments, the present invention relates to compounds represented by formula I and any of the attendant definitions, wherein the compound is

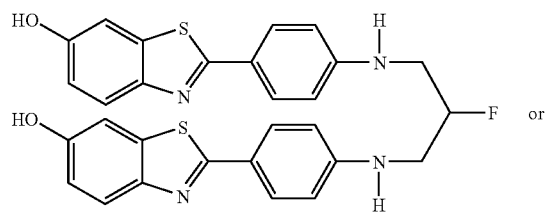

or

-continued

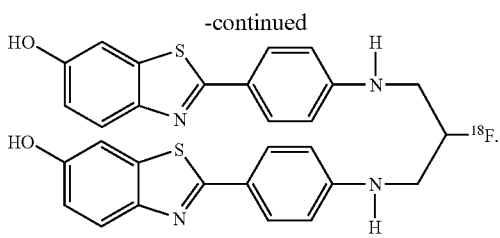

Selected Compositions of the Invention

One aspect of the present invention relates to a pharmaceutical composition comprising a pharmaceutically acceptable carrier; and a compound of formula I-IV, or a pharmaceutically acceptable salt thereof:

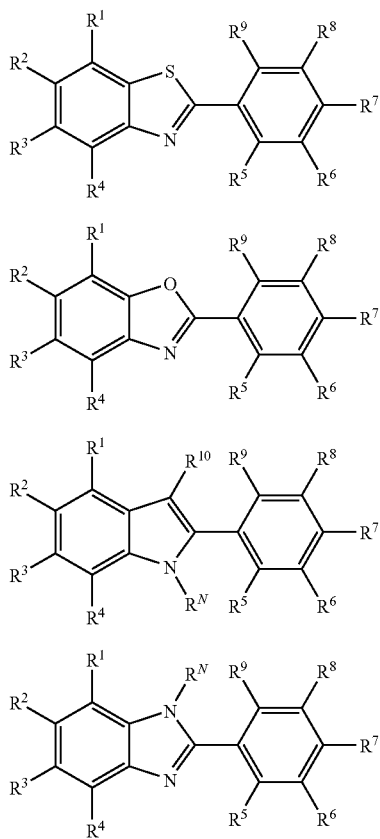

wherein, independently for each occurrence, $R^1$, $R^2$, $R^3$, $R^4$, $R^5$, $R^6$, $R^7$, $R^8$, $R^9$, and $R^{10}$ are hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —Y-(haloalkylene)-alkyl;

$R^N$ is hydrogen, lower alkyl, or -(haloalkylene)-alkyl;

Y is a bond, $N(R^N)$, O, or S;

provided that at least one of $R^1$, $R^2$, $R^3$, $R^4$, $R^5$, $R^6$, $R^7$, $R^8$, $R^9$, or $R^{10}$ is —Y-(haloalkylene)-alkyl; or $R^N$ is -(haloalkylene)-alkyl.

In certain embodiments, the present invention relates to the aforementioned pharmaceutical composition and any of the attendant definitions, wherein the compound is represented by formula I.

In certain embodiments, the present invention relates to the aforementioned pharmaceutical composition and any of the attendant definitions, wherein the compound is represented by formula II.

In certain embodiments, the present invention relates to the aforementioned pharmaceutical composition and any of the attendant definitions, wherein the compound is represented by formula III.

In certain embodiments, the present invention relates to the aforementioned pharmaceutical composition and any of the attendant definitions, wherein the compound is represented by formula IV.

In certain embodiments, the present invention relates to the aforementioned pharmaceutical composition and any of the attendant definitions, wherein $R^7$ is —Y-(haloalkylene)-alkyl.

In certain embodiments, the present invention relates to the aforementioned pharmaceutical composition and any of the attendant definitions, wherein $R^7$ is —Y-(fluoroalkylene)-alkyl.

In certain embodiments, the present invention relates to the aforementioned pharmaceutical composition and any of the attendant definitions, wherein $R^7$ is —Y-(monofluoroalkylene)-alkyl.

In certain embodiments, the present invention relates to the aforementioned pharmaceutical composition and any of the attendant definitions, wherein $R^7$ is —Y-(monofluoroalkylene)-alkyl; and said fluoro substituent is bound to a secondary alkylene carbon.

In certain embodiments, the present invention relates to the aforementioned pharmaceutical composition and any of the attendant definitions, wherein $R^7$ is —Y-(monofluoroalkylene)-alkyl; and said fluoro substituent is bound to a tertiary alkylene carbon.

In certain embodiments, the present invention relates to the aforementioned pharmaceutical composition and any of the attendant definitions, wherein $R^7$ is —Y—([F-18]fluoroalkylene)-alkyl.

In certain embodiments, the present invention relates to the aforementioned pharmaceutical composition and any of the attendant definitions, wherein $R^7$ is —Y—([F-18]monofluoroalkylene)-alkyl; and said [F-18]fluoro substituent is bound to a secondary alkylene carbon.

In certain embodiments, the present invention relates to the aforementioned pharmaceutical composition and any of the attendant definitions, wherein $R^7$ is —Y—([F-18]monofluoroalkylene)-alkyl; and said [F-18]fluoro substituent is bound to a tertiary alkylene carbon.

In certain embodiments, the present invention relates to the aforementioned pharmaceutical composition and any of the attendant definitions, wherein $R^7$ is —Y—($CH_2CH^{18}F$)—$CH_3$.

In certain embodiments, the present invention relates to the aforementioned pharmaceutical composition and any of the attendant definitions, wherein Y is $N(R^N)$.

In certain embodiments, the present invention relates to the aforementioned pharmaceutical composition and any of the attendant definitions, wherein $R^N$ is hydrogen.

In certain embodiments, the present invention relates to the aforementioned pharmaceutical composition and any of the attendant definitions, wherein $R^1$, $R^3$, $R^4$, $R^5$, $R^6$, $R^8$, and $R^9$ are hydrogen.

In certain embodiments, the present invention relates to the aforementioned pharmaceutical composition and any of the attendant definitions, wherein $R^2$ is hydroxy, alkoxy, aryloxy, heteroaryloxy, aralkyloxy, or heteroaralkyloxy.

In certain embodiments, the present invention relates to the aforementioned pharmaceutical composition and any of the attendant definitions, wherein $R^2$ is hydroxy.

In certain embodiments, the present invention relates to the aforementioned pharmaceutical composition and any of the attendant definitions, wherein $R^{10}$ is hydrogen.

In certain embodiments, the present invention relates to the aforementioned pharmaceutical composition and any of the attendant definitions, wherein the compound is represented by formula I; $R^7$ is —N(H)-(monofluoroalkylene)-$CH_3$; $R^1$, $R^3$, $R^4$, $R^5$, $R^6$, $R^8$ and $R^9$ are hydrogen; and $R^2$ is hydroxy.

In certain embodiments, the present invention relates to the aforementioned pharmaceutical composition and any of the attendant definitions, wherein the compound is represented by formula I; $R^7$ is —N(H)—([F-18]monofluoroalkylene)-$CH_3$; $R^1$, $R^3$, $R^4$, $R^5$, $R^6$, $R^8$, and $R^9$ are hydrogen; and $R^2$ is hydroxy.

In certain embodiments, the present invention relates to the aforementioned pharmaceutical composition and any of the attendant definitions, wherein the compound is represented by formula I; $R^7$ is —N(H)—($CH_2$CHF)—$CH_3$; $R^1$, $R^3$, $R^4$, $R^5$, $R^6$, $R^7$, and $R^8$ are hydrogen; and $R^2$ is hydroxy.

In certain embodiments, the present invention relates to the aforementioned pharmaceutical composition and any of the attendant definitions, wherein the compound is represented by formula I; $R^7$ is —N(H)—($CH_2CH^{18}F$)—$CH_3$; $R^1$, $R^3$, $R^4$, $R^5$, $R^6$, $R^8$, and $R^9$ are hydrogen; and $R^2$ is hydroxy.

In certain embodiments, the present invention relates to the aforementioned pharmaceutical composition and any of the attendant definitions, wherein the compound is

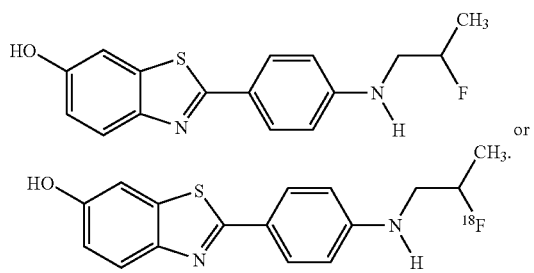

In certain embodiments, the present invention relates to the aforementioned pharmaceutical composition and any of the attendant definitions, wherein the pharmaceutical composition further comprises a sugar alcohol.

In certain embodiments, the present invention relates to the aforementioned pharmaceutical composition and any of the attendant definitions, wherein the pharmaceutical composition further comprises glycol, glycerol, erythritol, arabitol, xylitol, ribitol, mannitol, sorbitol, isomalt, maltitol, or lactitol.

In certain embodiments, the present invention relates to the aforementioned pharmaceutical composition and any of the attendant definitions, wherein the pharmaceutical composition further comprises mannitol.

Another aspect of the present invention relates to a pharmaceutical composition comprising a pharmaceutically acceptable carrier; and a compound of formula I-IV, or a pharmaceutically acceptable salt thereof:

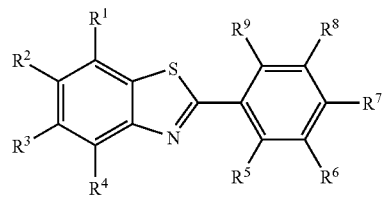

I

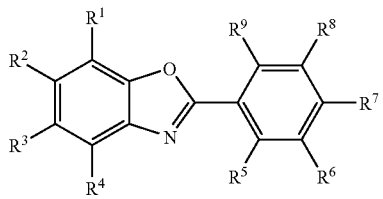

II

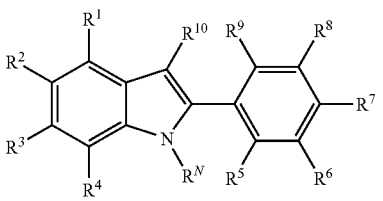

III

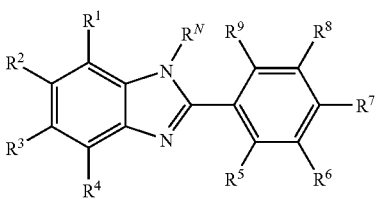

IV wherein, independently for each occurrence, $R^1$, $R^2$, $R^3$, $R^4$, $R^5$, $R^6$, $R^8$, $R^9$, and $R^{10}$ are hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, or isocyano;

$R^7$ is —Y-(haloalkylene)-R;

Y is a bond, $N(R^N)$, O, or S;

$R^N$ is hydrogen, or lower alkyl; and

R is

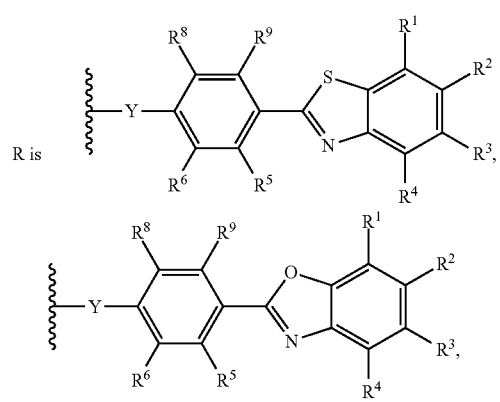

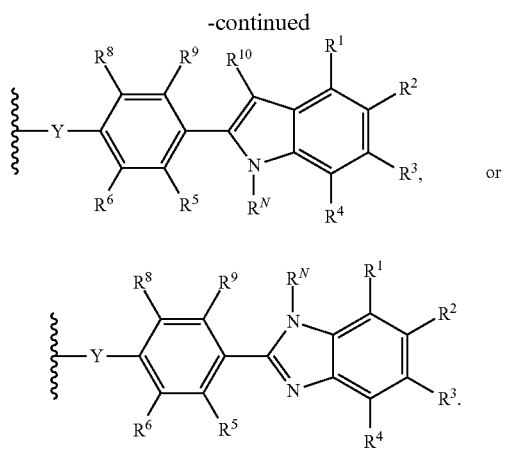

In certain embodiments, the present invention relates to the aforementioned pharmaceutical composition and any of the attendant definitions, wherein the compound is represented by formula I.

In certain embodiments, the present invention relates to the aforementioned pharmaceutical composition and any of the attendant definitions, wherein the compound is represented by formula II.

In certain embodiments, the present invention relates to the aforementioned pharmaceutical composition and any of the attendant definitions, wherein the compound is represented by formula III.

In certain embodiments, the present invention relates to the aforementioned pharmaceutical composition and any of the attendant definitions, wherein the compound is represented by formula IV.

In certain embodiments, the present invention relates to the aforementioned pharmaceutical composition and any of the attendant definitions, wherein $R^7$ is —Y-(haloalkylene)-Y—R.

In certain embodiments, the present invention relates to the aforementioned pharmaceutical composition and any of the attendant definitions, wherein $R^7$ is —Y-(fluoroalkylene)-Y—R.

In certain embodiments, the present invention relates to the aforementioned pharmaceutical composition and any of the attendant definitions, wherein $R^7$ is —Y-(monofluoroalkylene)-Y—R.

In certain embodiments, the present invention relates to the aforementioned pharmaceutical composition and any of the attendant definitions, wherein $R^7$ is —Y—([F-18]fluoroalkylene)-Y—R.

In certain embodiments, the present invention relates to the aforementioned pharmaceutical composition and any of the attendant definitions, wherein $R^7$ is —Y—([F-18]monofluoroalkylene)-Y—R.

In certain embodiments, the present invention relates to the aforementioned pharmaceutical composition and any of the attendant definitions, wherein Y is $N(R^N)$.

In certain embodiments, the present invention relates to the aforementioned pharmaceutical composition and any of the attendant definitions, wherein $R^N$ is hydrogen.

In certain embodiments, the present invention relates to the aforementioned pharmaceutical composition and any of the attendant definitions, wherein $R^7$ is —N(H)-(haloalkylene)-N(H)—R.

In certain embodiments, the present invention relates to the aforementioned pharmaceutical composition and any of the attendant definitions, wherein $R^1$, $R^3$, $R^4$, $R^5$, $R^6$, $R^8$, and $R^9$ are hydrogen.

In certain embodiments, the present invention relates to the aforementioned pharmaceutical composition and any of the attendant definitions, wherein $R^2$ is hydroxy, alkoxy, aryloxy, heteroaryloxy, aralkyloxy, or heteroaralkyloxy.

In certain embodiments, the present invention relates to the aforementioned pharmaceutical composition and any of the attendant definitions, wherein $R^2$ is hydroxy.

In certain embodiments, the present invention relates to the aforementioned pharmaceutical composition and any of the attendant definitions, wherein $R^{10}$ is hydrogen.

In certain embodiments, the present invention relates to the aforementioned pharmaceutical composition and any of the attendant definitions, wherein the compound is represented by formula I; $R^7$ is —Y-(haloalkylene)-Y—R; and R is

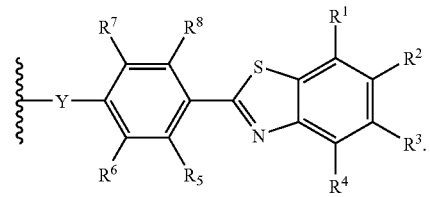

In certain embodiments, the present invention relates to the aforementioned pharmaceutical composition and any of the attendant definitions, wherein the compound is represented by formula II; wherein $R^7$ is —Y-(haloalkylene)-Y—R; and R is

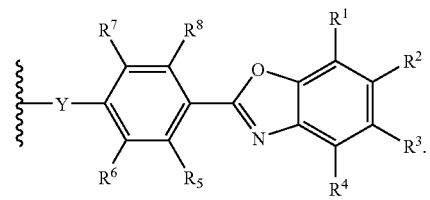

In certain embodiments, the present invention relates to the aforementioned pharmaceutical composition and any of the attendant definitions, wherein the compound is represented by formula III; $R^7$ is —Y-(haloalkylene)-Y—R; and R is

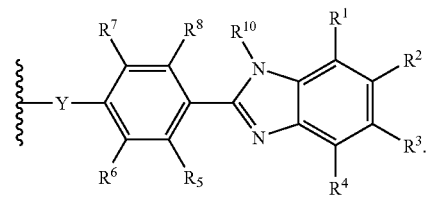

In certain embodiments, the present invention relates to the aforementioned pharmaceutical composition and any of the attendant definitions, wherein the compound is represented by formula IV; wherein $R^7$ is —Y-(haloalkylene)-Y—R; and R is

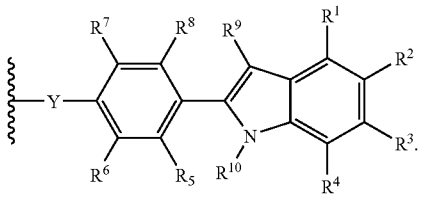

In certain embodiments, the present invention relates to the aforementioned pharmaceutical composition and any of the attendant definitions, wherein the compound is represented by formula I; wherein $R^7$ is —N(H)-(monofluoroalkylene)-N(H)—R; R is

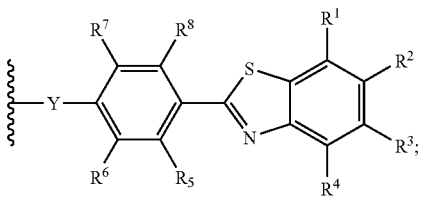

$R^1$, $R^3$, $R^4$, $R^5$, $R^6$, $R^8$, and $R^9$ are hydrogen; and $R^2$ is hydroxy.

In certain embodiments, the present invention relates to the aforementioned pharmaceutical composition and any of the attendant definitions, wherein the compound is represented by formula I; $R^7$ is —N(H)—([F-18]monofluoroalkylene)-N(H)—R; R is

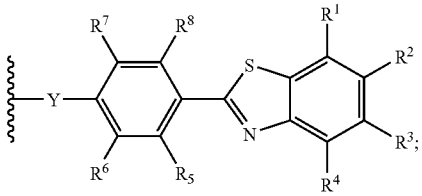

$R^1$, $R^3$, $R^4$, $R^5$, $R^6$, $R^8$, and $R^9$ are hydrogen; and $R^2$ is hydroxy.

In certain embodiments, the present invention relates to the aforementioned pharmaceutical composition and any of the attendant definitions, wherein the compound is represented by formula I; $R^7$ is —N(H)—(CH$_2$CHFCH$_2$)—N(H)—R; R is

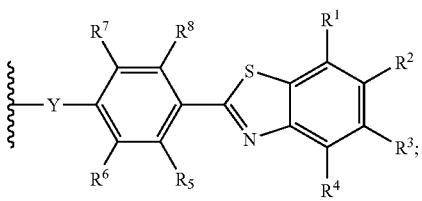

$R^1$, $R^3$, $R^4$, $R^5$, $R^6$, $R^8$, and $R^9$ are hydrogen; and $R^2$ is hydroxy.

In certain embodiments, the present invention relates to the aforementioned pharmaceutical composition and any of the attendant definitions, wherein the compound is represented by formula I; wherein $R^7$ is —N(H)—(CH$_2$CH$^{18}$FCH$_2$)—N(H)—R; R is

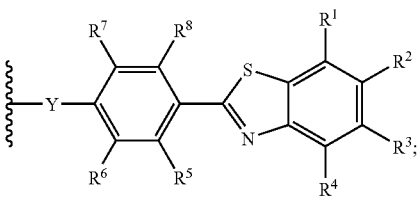

$R^1$, $R^3$, $R^4$, $R^5$, $R^6$, $R^8$, and $R^9$ are hydrogen; and $R^2$ is hydroxy.

In certain embodiments, the present invention relates to the aforementioned pharmaceutical composition and any of the attendant definitions, wherein the compound is

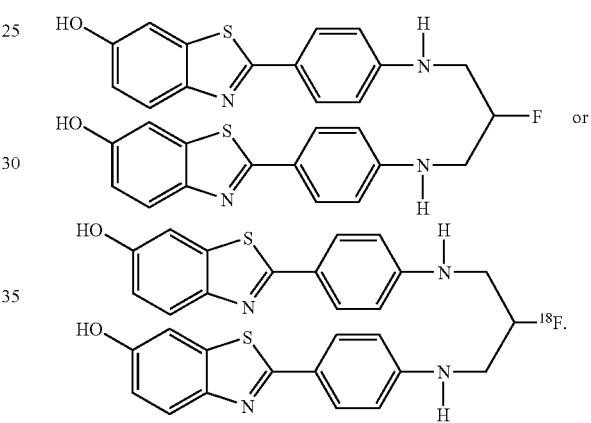

In certain embodiments, the present invention relates to the aforementioned pharmaceutical composition and any of the attendant definitions, wherein the pharmaceutical composition further comprises a sugar alcohol.

In certain embodiments, the present invention relates to the aforementioned pharmaceutical composition and any of the attendant definitions, wherein the pharmaceutical composition further comprises glycol, glycerol, erythritol, arabitol, xylitol, ribitol, mannitol, sorbitol, isomalt, maltitol, or lactitol.

In certain embodiments, the present invention relates to the aforementioned pharmaceutical composition and any of the attendant definitions, wherein the pharmaceutical composition further comprises mannitol.

Selected Methods of the Invention

One aspect of the invention relates to a method for amyloid imaging a subject suffering from an amylodiosis-associated pathological condition, or treating a subject suffering from an amylodiosis-associated pathological condition, comprising the step of:

administering a compound, or a composition comprising a pharmaceutically acceptable carrier and the compound or a pharmaceutically acceptable salt thereof, to the subject, wherein the compound is represented by formula I-IV:

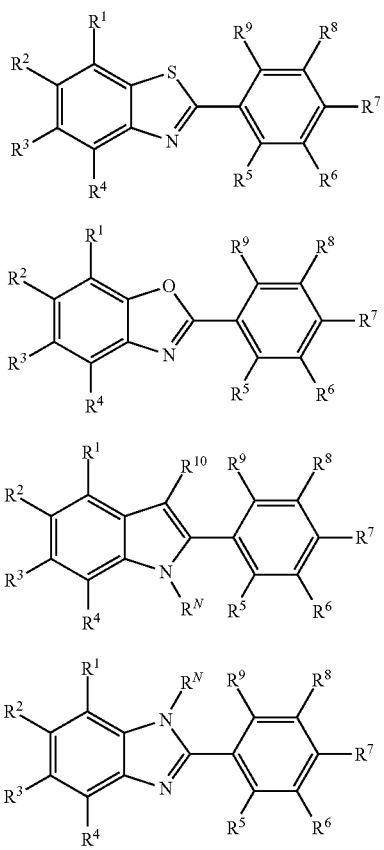

wherein, independently for each occurrence,

R¹, R², R³, R⁴, R⁵, R⁶, R⁷, R⁸, R⁹, and R¹⁰ are hydrogen, halo, azido, alkyl, haloalkyl, perhaloalkyl, fluoroalkyl, perfluoroalkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, acyloxy, silyl, thioether, sulfo, sulfonate, sulfonyl, sulfonamido, formyl, cyano, isocyano, or —Y-(haloalkylene)-alkyl;

$R^N$ is hydrogen, lower alkyl, or -(haloalkylene)-alkyl;

Y is a bond, $N(R^N)$, O, or S;

provided that at least one of R¹, R², R³, R⁴, R⁵, R⁶, R⁷, R⁸, R⁹, or R¹⁰ is —Y-(haloalkylene)-alkyl; or $R^N$ is -(haloalkylene)-alkyl.

In certain embodiments, the present invention relates to the aforementioned method and any of the attendant definitions, wherein the compound is represented by formula I.

In certain embodiments, the present invention relates to the aforementioned method and any of the attendant definitions, wherein the compound is represented by formula II.

In certain embodiments, the present invention relates to the aforementioned method and any of the attendant definitions, wherein the compound is represented by formula III.

In certain embodiments, the present invention relates to the aforementioned method and any of the attendant definitions, wherein the compound is represented by formula IV.

In certain embodiments, the present invention relates to the aforementioned method and any of the attendant definitions, wherein R⁷ is —Y-(haloalkylene)-alkyl.

In certain embodiments, the present invention relates to the aforementioned method and any of the attendant definitions, wherein R⁷ is —Y-(fluoroalkylene)-alkyl.

In certain embodiments, the present invention relates to the aforementioned method and any of the attendant definitions, wherein R⁷ is —Y-(monofluoroalkylene)-alkyl.

In certain embodiments, the present invention relates to the aforementioned method and any of the attendant definitions, wherein R⁷ is —Y-(monofluoroalkylene)-alkyl; and said fluoro substituent is bound to a secondary alkylene carbon.

In certain embodiments, the present invention relates to the aforementioned method and any of the attendant definitions, wherein R⁷ is —Y-(monofluoroalkylene)-alkyl; and said fluoro substituent is bound to a tertiary alkylene carbon.

In certain embodiments, the present invention relates to the aforementioned method and any of the attendant definitions, wherein R⁷ is —Y—([F-18]fluoroalkylene)-alkyl.

In certain embodiments, the present invention relates to the aforementioned method and any of the attendant definitions, wherein R⁷ is —Y—([F-18]monofluoroalkylene)-alkyl; and said [F-18]fluoro substituent is bound to a secondary alkylene carbon.

In certain embodiments, the present invention relates to the aforementioned method and any of the attendant definitions, wherein R⁷ is —Y—([F-18]monofluoroalkylene)-alkyl; and said [F-18]fluoro substituent is bound to a tertiary alkylene carbon.

In certain embodiments, the present invention relates to the aforementioned method and any of the attendant definitions, wherein R⁷ is —Y—$(CH_2CH^{18}F)$—$CH_3$.

In certain embodiments, the present invention relates to the aforementioned method and any of the attendant definitions, wherein Y is $N(R^N)$.

In certain embodiments, the present invention relates to the aforementioned method and any of the attendant definitions, wherein $R^N$ is hydrogen.

In certain embodiments, the present invention relates to the aforementioned method and any of the attendant definitions, wherein R¹, R³, R⁴, R⁵, R⁶, R⁸, and R⁹ are hydrogen.

In certain embodiments, the present invention relates to the aforementioned method and any of the attendant definitions, wherein R² is hydroxy, alkoxy, aryloxy, heteroaryloxy, aralkyloxy, or heteroaralkyloxy.

In certain embodiments, the present invention relates to the aforementioned method and any of the attendant definitions, wherein R² is hydroxy.

In certain embodiments, the present invention relates to the aforementioned method and any of the attendant definitions, wherein R¹⁰ is hydrogen.

In certain embodiments, the present invention relates to the aforementioned method and any of the attendant definitions, wherein the compound is represented by formula I; R⁷ is —N(H)-(monofluoroalkylene)-$CH_3$; R¹, R³, R⁴, R⁵, R⁶, R⁸ and R⁹ are hydrogen; and R² is hydroxy.

In certain embodiments, the present invention relates to the aforementioned method and any of the attendant definitions, wherein the compound is represented by formula I; R⁷ is —N(H)—([F-18]monofluoroalkylene)-$CH_3$; R¹, R³, R⁴, R⁵, R⁶, R⁸ and R⁹ are hydrogen; and R² is hydroxy.

In certain embodiments, the present invention relates to the aforementioned method and any of the attendant definitions, wherein the compound is represented by formula I; R⁷ is —N(H)—$(CH_2CHF)$—$CH_3$; R¹, R³, R⁴, R⁵, R⁶, R⁷, and R⁸ are hydrogen; and R² is hydroxy.

In certain embodiments, the present invention relates to the aforementioned method and any of the attendant definitions, wherein the compound is represented by formula I; R⁷ is —N(H)—(CH₂CH¹⁸F)—CH₃; $R^1, R^3, R^4, R^5, R^6, R^8$, and $R^9$ are hydrogen; and $R^2$ is hydroxy.

In certain embodiments, the present invention relates to the aforementioned method and any of the attendant definitions, wherein the compound is

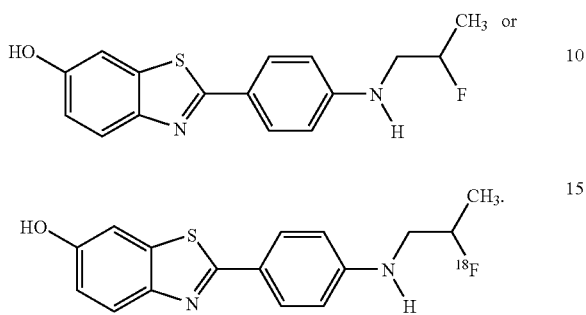

In certain embodiments, the present invention relates to the aforementioned method and any of the attendant definitions, wherein the pharmaceutical composition further comprises a sugar alcohol.

In certain embodiments, the present invention relates to the aforementioned method and any of the attendant definitions, wherein the pharmaceutical composition further comprises glycol, glycerol, erythritol, arabitol, xylitol, ribitol, mannitol, sorbitol, isomalt, maltitol, or lactitol.

In certain embodiments, the present invention relates to the aforementioned method and any of the attendant definitions, wherein the pharmaceutical composition further comprises mannitol.

Another aspect of the invention relates to a method for amyloid imaging a subject suffering from an amylodiosis-associated pathological condition, or treating a subject suffering from an amylodiosis-associated pathological condition, comprising the step of:

administering a compound, or a composition comprising a pharmaceutically acceptable carrier and the compound or a pharmaceutically acceptable salt thereof, to the subject, wherein the compound is represented by formula I-IV:

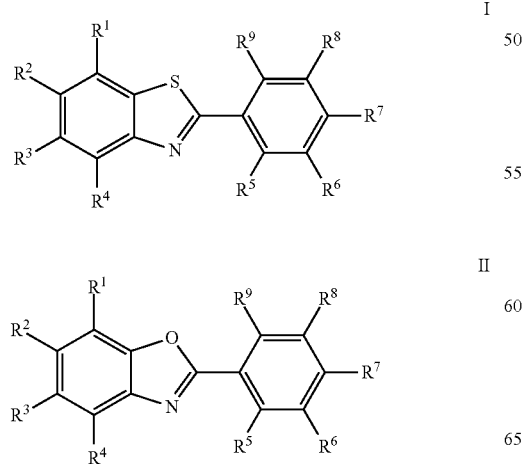

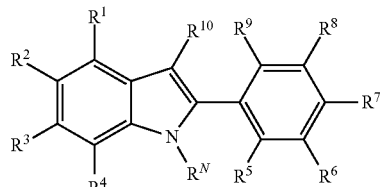

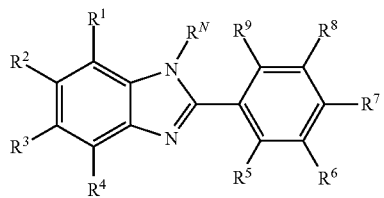

wherein, independently for each occurrence, $R^1, R^2, R^3, R^4, R^5, R^6, R^8, R^9$, and $R^{10}$ are hydrogen, halo, azido, alkyl, haloalkyl, perhaloalkyl, fluoroalkyl, perfluoro-alkyl, aralkyl, alkenyl, alkynyl, cycloalkyl, heterocyclyl, aryl, heteroaryl, aralkyl, heteroaralkyl, hydroxy, alkoxy, aryloxy, heteroaryloxy, aralkyloxy, heteroaralkyloxy, amino, alkylamino, arylamino, acylamino, heteroarylamino, nitro, sulfhydryl, imino, amido, phosphonate, phosphinate, acyl, carboxyl, oxycarbonyl, aryloxy, silyl, thioether, sulfo, sulfonate, sulfonyl, sulfonamido, formyl, cyano, or isocyano;

$R^7$ is —Y-(haloalkylene)-R;

Y is a bond, N($R^N$), O, or S;

$R^N$ is hydrogen, or lower alkyl; and

R is

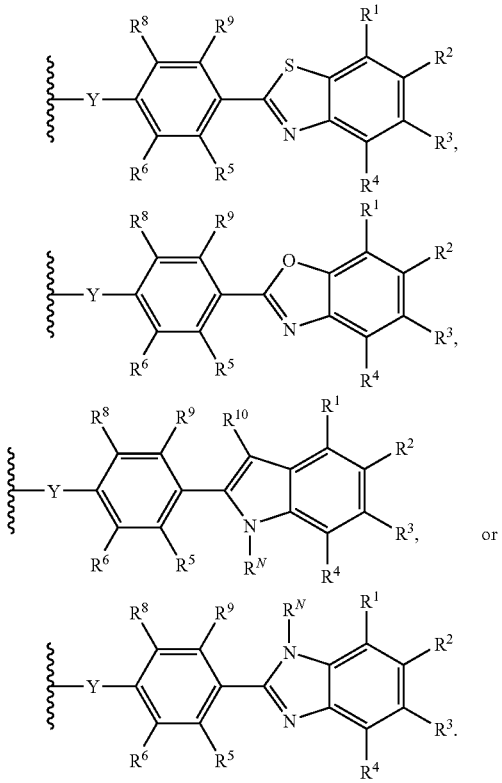

In certain embodiments, the present invention relates to the aforementioned method and any of the attendant definitions, wherein the compound is represented by formula I.

In certain embodiments, the present invention relates to the aforementioned method and any of the attendant definitions, wherein the compound is represented by formula II.

In certain embodiments, the present invention relates to the aforementioned method and any of the attendant definitions, wherein the compound is represented by formula III.

In certain embodiments, the present invention relates to the aforementioned method and any of the attendant definitions, wherein the compound is represented by formula IV.

In certain embodiments, the present invention relates to the aforementioned method and any of the attendant definitions, wherein $R^7$ is —Y-(haloalkylene)-Y—R.

In certain embodiments, the present invention relates to the aforementioned method and any of the attendant definitions, wherein $R^7$ is —Y-(fluoroalkylene)-Y—R.

In certain embodiments, the present invention relates to the aforementioned method and any of the attendant definitions, wherein $R^7$ is —Y-(monofluoroalkylene)-Y—R.

In certain embodiments, the present invention relates to the aforementioned method and any of the attendant definitions, wherein $R^7$ is —Y—([F-18]fluoroalkylene)-Y—R.

In certain embodiments, the present invention relates to the aforementioned method and any of the attendant definitions, wherein $R^7$ is —Y—([F-18]monofluoroalkylene)-Y—R.

In certain embodiments, the present invention relates to the aforementioned method and any of the attendant definitions, wherein Y is $N(R^N)$.

In certain embodiments, the present invention relates to the aforementioned method and any of the attendant definitions, wherein $R^N$ is hydrogen.

In certain embodiments, the present invention relates to the aforementioned method and any of the attendant definitions, wherein $R^7$ is —N(H)-(haloalkylene)-N(H)—R.

In certain embodiments, the present invention relates to the aforementioned method and any of the attendant definitions, wherein $R^1$, $R^3$, $R^4$, $R^5$, $R^6$, $R^6$, $R^8$, and $R^9$ are hydrogen.

In certain embodiments, the present invention relates to the aforementioned method and any of the attendant definitions, wherein $R^2$ is hydroxy, alkoxy, aryloxy, heteroaryloxy, aralkyloxy, or heteroaralkyloxy.

In certain embodiments, the present invention relates to the aforementioned method and any of the attendant definitions, wherein $R^2$ is hydroxy.

In certain embodiments, the present invention relates to the aforementioned method and any of the attendant definitions, wherein $R^{10}$ is hydrogen.

In certain embodiments, the present invention relates to the aforementioned method and any of the attendant definitions, wherein the compound is represented by formula I; $R^7$ is —Y-(haloalkylene)-Y—R; and R is

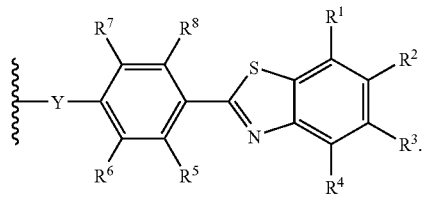

In certain embodiments, the present invention relates to the aforementioned method and any of the attendant definitions, wherein the compound is represented by formula II; wherein $R^7$ is —Y-(haloalkylene)-Y—R; and R is

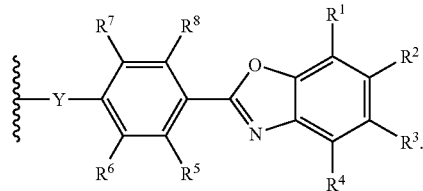

In certain embodiments, the present invention relates to the aforementioned method and any of the attendant definitions, wherein the compound is represented by formula III; $R^7$ is —Y-(haloalkylene)-Y—R; and R is

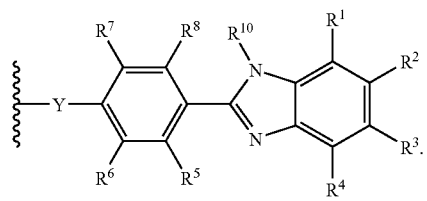

In certain embodiments, the present invention relates to the aforementioned method and any of the attendant definitions, wherein the compound is represented by formula IV; wherein $R^7$ is —Y-(haloalkylene)-Y—R; and R is

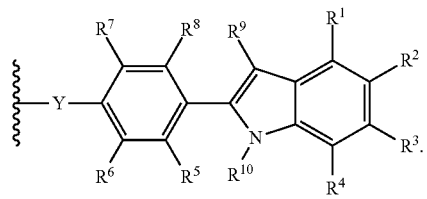

In certain embodiments, the present invention relates to the aforementioned method and any of the attendant definitions, wherein the compound is represented by formula I; wherein $R^7$ is —N(H)-(monofluoroalkylene)-N(H)—R; R is

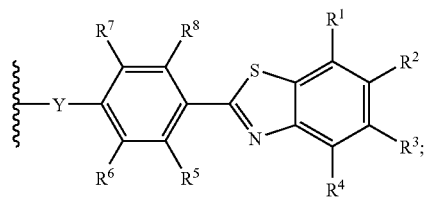

$R^1$, $R^3$, $R^4$, $R^5$, $R^6$, $R^8$, and $R^9$ are hydrogen; and $R^2$ is hydroxy.

In certain embodiments, the present invention relates to the aforementioned method and any of the attendant definitions, wherein the compound is represented by formula I; $R^7$ is —N(H)—([F-18]monofluoroalkylene)-N(H)—R; R is

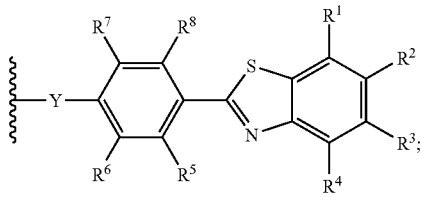

R$^1$, R$^3$, R$^4$, R$^5$, R$^6$, R$^8$, and R$^9$ are hydrogen; and R$^2$ is hydroxy.

In certain embodiments, the present invention relates to the aforementioned method and any of the attendant definitions, wherein the compound is represented by formula I; R$^7$ is —N(H)—(CH$_2$CHFCH$_2$)—N(H)—R; R is

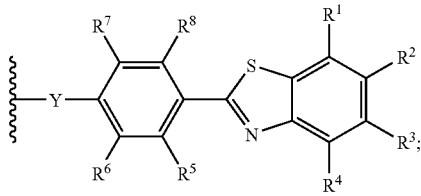

R$^1$, R$^3$, R$^4$, R$^5$, R$^6$, R$^8$, and R$^9$ are hydrogen; and R$^2$ is hydroxy.

In certain embodiments, the present invention relates to the aforementioned method and any of the attendant definitions, wherein the compound is represented by formula I; wherein R$^7$ is —N(H)—(CH$_2$CH$^{18}$FCH$_2$)—N(H)—R; R is

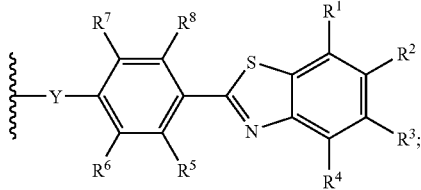

R$^1$, R$^3$, R$^4$, R$^5$, R$^6$R$^8$, and R$^9$ are hydrogen; and R$^2$ is hydroxy.

In certain embodiments, the present invention relates to the aforementioned method and any of the attendant definitions, wherein the compound is

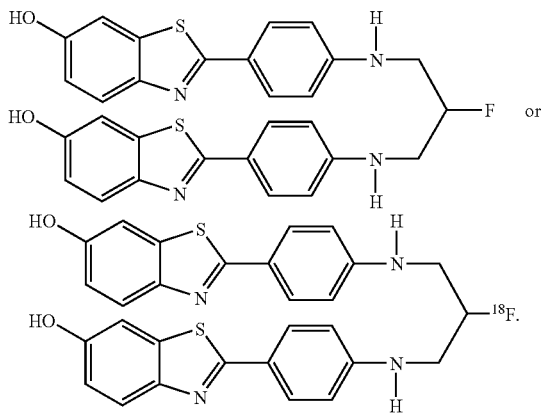

In certain embodiments, the present invention relates to the aforementioned method and any of the attendant definitions, wherein the pharmaceutical composition further comprises a sugar alcohol.

In certain embodiments, the present invention relates to the aforementioned method and any of the attendant definitions, wherein the pharmaceutical composition further comprises glycol, glycerol, erythritol, arabitol, xylitol, ribitol, mannitol, sorbitol, isomalt, maltitol, or lactitol.

In certain embodiments, the present invention relates to the aforementioned method and any of the attendant definitions, wherein the pharmaceutical composition further comprises mannitol.

Definitions

Herein a number of terms are used extensively. The following definitions are provided to facilitate understanding of the invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure. As used herein, "fluoroalkyl" denotes an alkyl where one or more hydrogens have been replaced with fluorines; "perfluoroalkyl" denotes an alkyl where all the hydrogens have been replaced with fluorines.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "alkylene," is art-recognized, and as used herein, pertains to a bidentate moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated. Examples of linear saturated $C_{1-10}$alkylene groups include, but are not limited to, —($CH_2$)$_n$— where n is an integer from 1 to 10, for example, —$CH_2$— (methylene), —$CH_2CH_2$-(ethylene), —$CH_2CH_2CH_2$— (propylene), —$CH_2CH_2CH_2CH_2$— (butylene), —$CH_2CH_2CH_2CH_2CH_2$-(pentylene) and —$CH_2CH_2CH_2CH_2CH_2CH_2$— (hexylene). Examples of branched saturated $C_{1-10}$alkylene groups include, but are not limited to, —CH($CH_3$)—, —CH($CH_3$)$CH_2$—, —CH($CH_3$)$CH_2CH_2$—, —CH($CH_3$)$CH_2CH_2CH_2$—, —$CH_2$CH($CH_3$)$CH_2$—, —$CH_2$CH($CH_3$)$CH_2CH_2$—, —CH($CH_2CH_3$)—, —CH($CH_2CH_3$)$CH_2$—, and —$CH_2$CH($CH_2CH_3$)$CH_2$—. Examples of linear partially unsaturated $C_{1-10}$alkylene groups include, but are not limited to, —CH=CH— (vinylene), —CH=CH—$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—CH=CH—$CH_2$—$CH_2$—, —CH=CH—$CH_2$—CH=CH—, and —CH=CH—$CH_2$—$CH_2$—CH=CH—. Examples of branched partially unsaturated $C_{1-10}$alkylene groups include, but are not limited to, —C($CH_3$)=CH—, —C($CH_3$)=CH—$CH_2$—, and —CH=CH—CH($CH_3$)—. Examples of alicyclic saturated $C_{1-10}$alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-10}$alkylene groups include, but are not limited to, cyclopentenylene (e.g., 4-cyclopenten-1,3-ylene), and cyclohexenylene (e.g., 2-cyclohexen-1,4-ylene, 3-cyclohexen-1,2-ylene, and 2,5-cyclohexadien-1,4-ylene).

The term "haloalkylene," as used herein, pertains to a bidentate alkylene moiety as described above wherein at least one hydrogen atom has been replaced by a halogen. The term "fluoroalkylene," as used herein, pertains to a bidentate alkylene moiety as described above wherein at least one hydrogen atom has been replaced by a fluorine. The term "monofluoroalkylene," as used herein, pertains to a bidentate alkylene moiety as described above wherein only one hydrogen atom has been replaced by a fluorine. The term "[F-18]fluoroalkylene," as used herein, pertains to a bidentate alkylene moiety as described above wherein at least one hydrogen atom has been replaced by a F-18. The term "[F-18]monofluoroalkylene," as used herein, pertains to a bidentate alkylene moiety as described above wherein only one hydrogen atom has been replaced by a F-18.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, alkylthio, sulfonyl, sulfonamido, ketone, aldehyde, ester, heterocyclyl, aromatic or heteroaromatic moieties, trifluoromethyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on page 560 of "Advanced Inorganic Chemistry" by Cotton and Wilkinson, that is, for example, monovalent anionic groups sufficiently electronegative to exhibit a positive Hammett sigma value at least equaling that of a halide (e.g., CN, OCN, SCN, SeCN, TeCN, N$_3$, and C(CN)$_3$).

The terms "amine" and "amino" are art-recognized and refer to both unsubstituted and substituted amines, e.g., a moiety that may be represented by the general formulas:

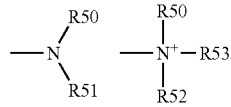

wherein R50, R51, R52 and R53 each independently represent a hydrogen, an alkyl, an alkenyl, —(CH$_2$)$_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

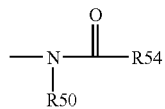

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

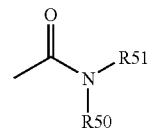

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

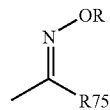

wherein R75 is hydrogen, alkyl, cycloalkyl, alkenyl, alkynyl, aryl, aralkyl, or —(CH$_2$)$_m$—R61. The moiety is an "oxime"

when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

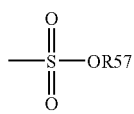

in which R57 is an electron pair, hydrogen, alkyl, cycloalkyl, or aryl.

The term "sulfate" is art recognized and includes a moiety that may be represented by the general formula:

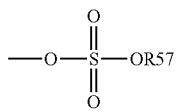

in which R57 is as defined above.

The term "sulfonamido" is art recognized and includes a moiety that may be represented by the general formula:

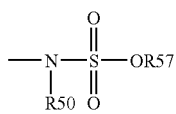

in which R50 and R56 are as defined above.

The term "sulfamoyl" is art-recognized and refers to a moiety that may be represented by the general formula:

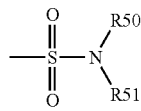

in which R50 and R51 are as defined above.

The term "sulfonyl" is art-recognized and refers to a moiety that may be represented by the general formula:

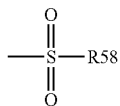

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

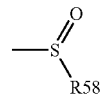

in which R58 is defined above.

The term "phosphoryl" is art-recognized and may in general be represented by the formula:

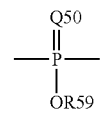

wherein Q50 represents S or O, and R59 represents hydrogen, a lower alkyl or an aryl. When used to substitute, e.g., an alkyl, the phosphoryl group of the phosphorylalkyl may be represented by the general formulas:

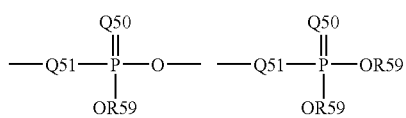

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

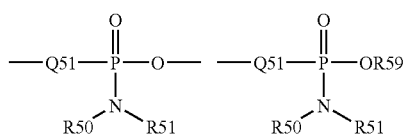

wherein Q51, R50, R51 and R59 are as defined above.

The term "phosphonamidite" is art-recognized and may be represented in the general formulas:

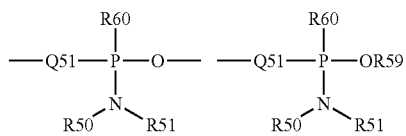

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

As used herein, the term "subject" or "individual" refers to a human or other vertebrate animal. It is intended that the term encompass "patients."

The term "diagnosis" as used herein refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, amount, or change in amount of which is indicative of the presence, severity, or absence of the condition.

The term "conjugated" refers to ionically or covalently attached (e.g., via a crosslinking agent).

A "chelating structure" refers to any molecule or complex of molecules that bind to both label and targeting moiety. Examples include $N_2S_2$ structure, a HYNIC (hydrazinonicotinic acid) group-containing structure, a 2-methylthiolnicotinic acid group containing structure, a carboxylate group-containing structure and the like.

A "radioimaging agent" refers to a composition capable of generating a detectable image upon binding with a target and shall include radionuclides such as, for example, $^{18}F$, $^{76}Br$, $^{77}Br$, $^{123}I$, $^{124}I$, $^{125}I$, $^{99m}Tc$, $^{68}Cu$, $^{64}Cu$ and $^{68}Ga$.

A "fluorescence imaging agent" refers to a composition capable of generating a detectable optical imaging upon binding with a target with or without specific wave length of light activation and shall include fluorophores. The preferred fluorescence agents are near infra red light absorbing agents.

A "target" refers to an in vivo site to which imaging compounds binds. A preferred target is a brain tissue from a subject suffering from AD or an amyloidosis-associated pathological condition. A "targeting molecule" is any molecule or biological entity that specifically accumulates in brain tissue from a subject suffering from AD or an amyloidosis-associated pathological condition.

As used herein, "pharmaceutically-acceptable carrier" includes any and all solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The formulation used in the present invention may also contain stabilizers, preservatives, buffers, antioxidants, or other additives known to those of skill in the art. The use of such media and agents for pharmaceutically-active substances is well known in the art. Supplementary active compounds can also be incorporated into the imaging agent of the invention. The imaging agent of the invention may further be administered to an individual in an appropriate diluent or adjuvant, co-administered with enzyme inhibitors or in an appropriate carrier such as human serum albumin or liposomes. Pharmaceutically-acceptable diluents include sterile saline and other aqueous buffer solutions. Adjuvants contemplated herein include resorcinols, non-ionic surfactants such as polyoxyethylene oleyl ether and n-hexadecyl polyethylene ether. Enzyme inhibitors include pancreatic trypsin inhibitor, diethylpyrocarbonate, and trasylol. Liposomes inhibitors include water-in-oil-in-water CGF emulsions, as well as conventional liposomes (see *J. Neuroimmunol.* 1984, 7, 27).

A "sugar alcohol" (also known as a polyol, polyhydric alcohol, or polyalcohol), as used herein, is a hydrogenated form of carbohydrate, whose carbonyl group (aldehyde or ketone, reducing sugar) has been reduced to a primary or secondary hydroxyl group. Examples of sugar alcohols include glycol, glycerol, erythritol, arabitol, xylitol, ribitol, mannitol, sorbitol, isomalt, maltitol, and lactitol.

As described herein, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See *J. Pharm. Sci.* 1977, 66, 1-19.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, *J. Pham. Sci.* 1977., supra)

Preferably, the imaging agent of the present invention is administered intravenously, and the imaging agent will be formulated as a sterile, pyrogen-free, parenterally-acceptable aqueous solution. The preparation of such parenterally-acceptable solutions, having due regard to pH, isotonicity, stability, and the like, is within the skill in the art. A preferred formulation for intravenous injection should contain, in addition to the imaging agent, an isotonic vehicle such as Sodium Chloride Injection, Ringer's Injection, Dextrose Injection, Dextrose and Sodium Chloride Injection, Lactated Ringer's Injection, or other vehicle as known in the art.

The amount of imaging agent used for diagnostic purposes and the duration of the imaging study will depend upon the nature and severity of the condition being treated, on the nature of therapeutic treatments which the patient has undergone, and on the idiosyncratic responses of the patient. Ultimately, the attending physician will decide the amount of imaging agent to administer to each individual patient and the duration of the imaging study.

The diagnostic imaging amounts are preferably about 3 to 15 millicuries (mCi) for a 70 kg normal adult, more preferably being about 1-25 mCi for a 70 kg normal adult.

The ultimate solution form is preferably sterile. Sterilization can be accomplished by any art recognized technique, including but not limited to, addition of antibacterial of antifungal agents, for example, paraben, chlorobutanol, phenol, sorbic acid, thimerosal, and the like.

More specifically, the compounds that can be formulated into a pharmaceutical composition include a therapeutically-effective amount of the compound and a pharmaceutically-acceptable carrier. The therapeutically-effective amount of the compound and the specific pharmaceutically-acceptable carrier will vary depending upon, e.g., the age, weight, sex of the subject, the mode of administration, and the type of viral condition being treated.

In a particular aspect, the pharmaceutical composition which can be used includes the compounds of the present invention in effective unit dosage form. As used herein, the term "effective unit dosage" or "effective unit dose" is used herein to mean a predetermined amount sufficient to be effective against AD or the like. Examples include amounts that enable detecting and imaging of amyloid deposit(s) in vivo or in vitro, that yield acceptable toxicity and bioavailability levels for pharmaceutical use, and/or prevent cell degeneration and toxicity associated with fibril formation.

The pharmaceutical compositions may contain the compound used in the method of this invention in an amount of from 0.01 to 99% by weight of the total composition, preferably 0.1 to 80% by weight of the total composition. For oral administration, the compound is generally administered in an amount of 0.1 g/body to 15 g/body, preferably 0.5 g/body to 5 g/body. For intravenous injection, the dose may be about 0.1 to about 30 mg/kg/day, preferably about 0.5 to about 10 mg/kg/day. If applied topically as a liquid, ointment, or cream, the compound may be present in an amount of about 0.1 to about 50 mg/mL, preferably about 0.5 to 30 mg/mL of the composition. Fluorescence agents will be administered in several µg/kg to several mg/kg. For example, 1-10 mg/kg.

When the compounds according to the invention are formulated for injection, the dose may be presented in unit dose form in ampoules or in multi-dose containers with added pharmaceutically-acceptable adjuvants such as a preservative.

In addition, the compositions may take forms such as suspensions, solutions, or emulsions in oily or aqueous vehicles, and may contain formulating agents, such as suspending, stabilizing, or dispersing agents, isotonic agents and/or dissolving co-solvents conventionally cited in the pharmaceutical art.

For systemic administration, the daily dosage as employed for adult human treatment will range from about 0.1 mg/kg to about 150 mg/kg, preferably about 0.2 mg/kg to about 80 mg/kg.

Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include oils such as corn oil, buffers such as PBS, saline, polyethylene glycol, glycerin, polypropylene glycol, dimethylsulfoxide, an amide such as dimethylacetamide, a protein such as albumin, and a detergent, such as Tween 80, mono-, oligopolysaccharides, such as glucose, lactose, cyclodextrins and starch.

The pharmaceutical compositions may contain other active ingredients, such as antimicrobial agents and other adjuvants such as benzyl alcohol and phenol compounds and diluents conventionally used in the art.

It should be understood that the embodiments and examples described herein are given by way of illustration, not limitation. Various changes and modifications within the scope of the present invention will become apparent to those skilled in the art from the present description.

EXEMPLIFICATION

It should be understood that the above-described embodiments and the following examples are given by way of illustration, not limitation. Various changes and modifications within the scope of the present invention will become apparent to those skilled in the art from the present description.

Example 1

Synthesis of [N-2[18F]fluoropropyl]-2-(4'-(methylamino)phenyl)-6-hydroxythiazole

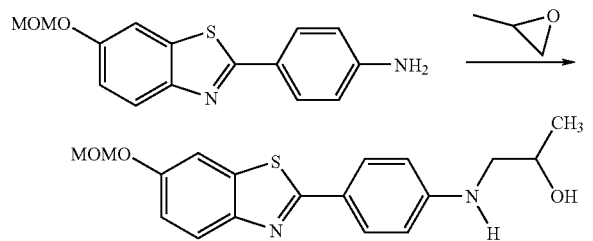

2-(4'-Aminophenyl)-6-methoxymethoxybenzothiazole (6-MOMO-BTA-O) was prepared according to a known procedure. See Mathis, C. A. et. al., *J. Med. Chem.* 2003, 46, 2470-2754. 6-MOMO-BTA-O (500 mg, 1.7 mmol), propylene oxide (500 mg, 8.5 mmol) and NaH (8 1 mg, 2 mmol, 60% oil dispersion) were heated at 100° C. in acetonitrile (30 mL) for 4 hr. The reaction mixture was poured over ice water (50 mL) and extracted with ether (3×20 mL). The combined extracts were dried (Na$_2$S0$_4$) and solvent was evaporated. Chromatography on silica gel using 50/50 ethyl acetatehexane gave 147 mg (43%) of the isopropanol derivative.

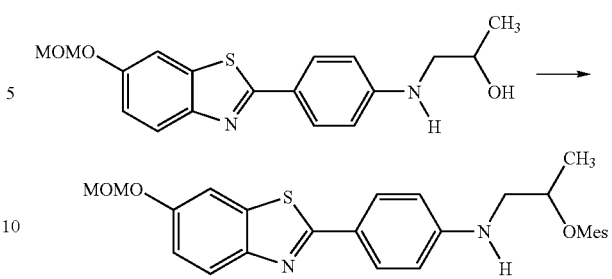

[N-2-propanol]-2-(4'-methylaminophenyl)-6-methoxymethoxybenzothiazole (100 mg, 0.29 mmol) and pyridine (0.5 mL) in methylene chloride (20 mL) was treated with methanesulfonyl chloride (0.66 mg, 58 mmol) for 4 hr. The mixture was washed with saturated NaHCO$_3$ (30 mL) and the organic layer was dried. After removal of volatiles by vacuum, the crude oil was chromatographed on silica gel using methylene chloride1 methanol (95:5) to give 50 mg (41%) of the mesylate.

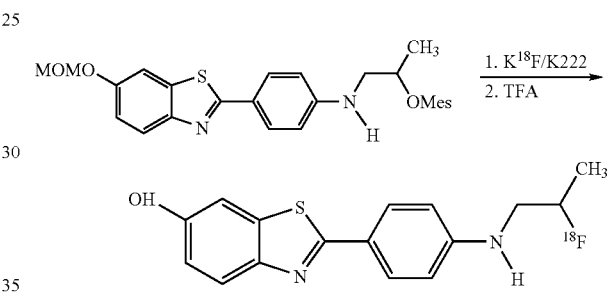

The mesylate (5 mg) in acetonitrile (1.00 mL) was added to a sealed vial containing dried K$^{18}$F/kryptofix (100 mCi) and heated at 120° C. for 10 min. Once cooled, the mixture was purified on a Silica SepPak using 10% methanol in methylene chloride. After solvent removal, the intermediate was treated with TFA at 100° C. for 10 min and solvent was removed by a nitrogen stream. The F-18 labeled derivative was dissolved in PBS/acetonitrile and purified on a C-18 column. [N-2[18F]fluoropropyl]-2-(4'-(methylamino)phenyl)-6-hydroxythiazole (10 mCi) was prepared within 90 min with 98% radiochemical purity.

See also the "Synthesis Examples" in International Application No. PCT/US2005/023618, hereby incorporated by reference.

Example 2

Synthesis of a Dimer of [N-2[18F]fluoropropyl]-2-(4'-(methylamino)phenyl)-6-hydroxythiazole The dimer series relating to the structure of [N-2[18F]fluoropropyl]-2-(4'-(methylamino)phenyl)-6-hydroxythiazole (F-18 MPHT) can be synthesized according to the scheme as illustrated in FIG. 1.

Alternatively the synthesis of a 2-[F18]fluoropropane dimer of 2-(4'-aminophenyl)-6-methoxymethoxybenzothiazole can be prepared as outlined below.

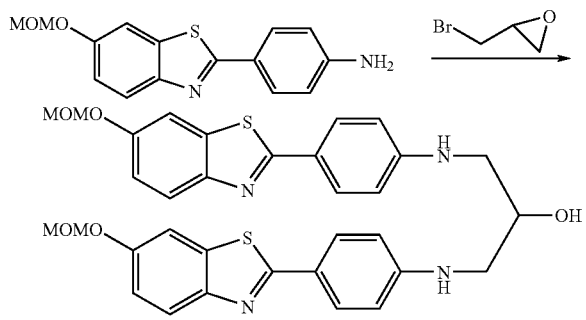

First, epibromohyrin and 2-(4'-aminophenyl)-6-methoxymethoxybenzothiazole is heated in acetonitrile and in the presence of lithium bromide (cat.) at 150° C. for 12 hr.

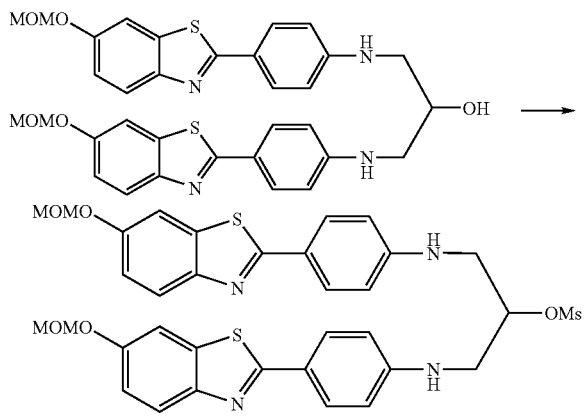

The resulting alcohol in pyridine and methylene chloride is then treated with methanesulfonyl chloride for 4 hr. The mixture is washed with saturated NaHCO$_3$ (30 mL) and the organic layer dried. After removal of volitiles by vacuum, the crude oil is chromatographed on silica gel using methylene chloride/methanol (95:5) to give the mesylate.

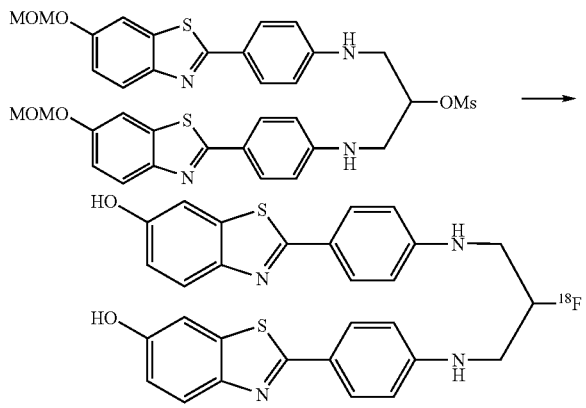

The mesylate (5 mg) in acetonitrile (100 μL) is added to a sealed vial containing dried K$^{18}$F/kryptofix (100 mCi) and heated at 120° C. for 10 min. Once cooled, the mixture is purified on a Silica SepPak using 10% methanol in methylene chloride. After solvent removal, the intermediate was treated with TFA at 100° C. for 10 min and solvent is removed by a nitrogen stream. The F-18 labeled derivative is dissolved in PBS/acetonitrile and purified on a C-18 column.

Example 3

In Vivo Studies

Nude mice positioned in a MicroPET camera were injected with 30-40 pCi per animal with the tracer and sequential imaging was performed for a period of 45 minutes.

Figure 2:
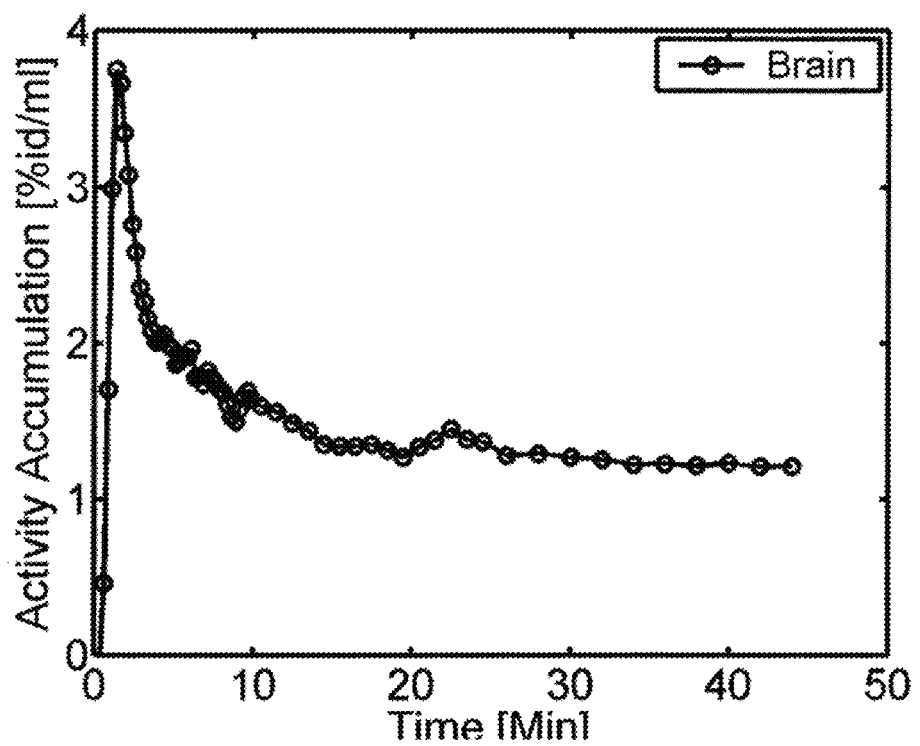
FIG. 2 depicts a graph showing the brain activity of a nude mouse after the first two minutes of injection of F-18MHT.
Figure 3:
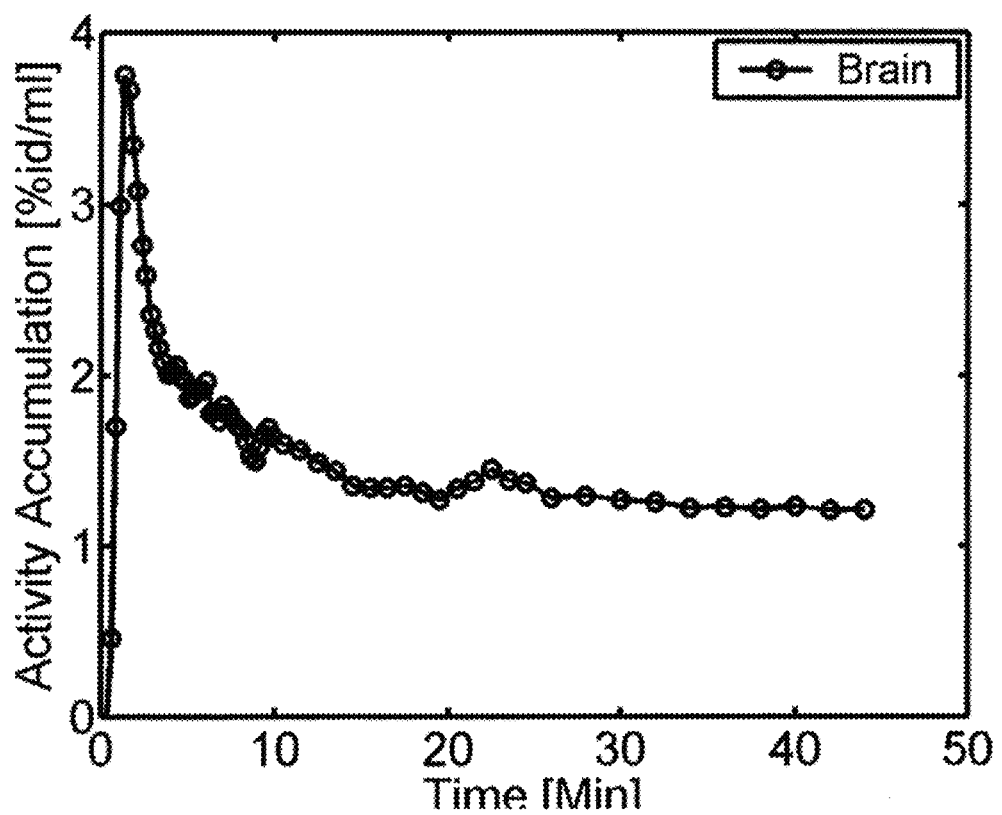
FIG. 3 shows the brain activity of a nude mouse after forty-five minutes of injection of F-18MHT.
Figure 4:
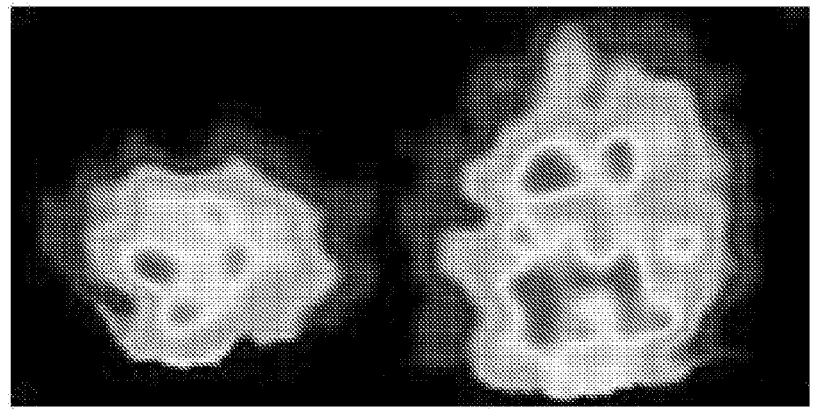
FIG. 4 shows clear visualization of the right and left brain hemispheres of the nude mouse after treatment with F-18MHT.

Brain activity was pronounced within the first 2 minutes (4% ID/g) (see FIG. 2) and washed out quickly; brain activity was 1.2% ID/g at 45 minutes (see FIG. 3). Right and left hemispheres were clearly visualized (see FIG. 4).

See also the "Biological Example" in International Application No. PCT/US2005/023618, hereby incorporated by reference.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound, wherein the compound is

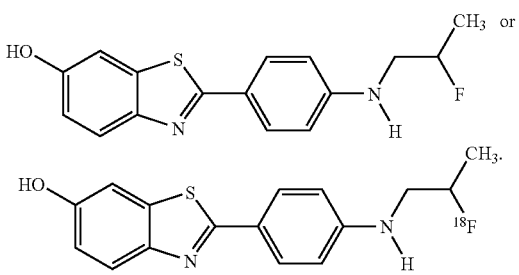

2. A pharmaceutical composition comprising a pharmaceutically acceptable carrier; and a compound, wherein the compound is

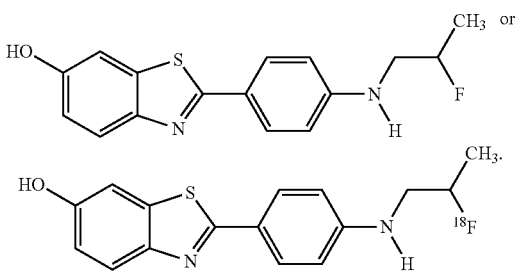

3. A method for amyloid imaging a subject suffering from an amyloidosis-associated pathological condition selected from Alzheimer's disease and senile dementia, comprising the step of:

administering a compound, or a pharmaceutical composition comprising the compound and a pharmaceutically acceptable carrier, to the subject;
wherein the compound is

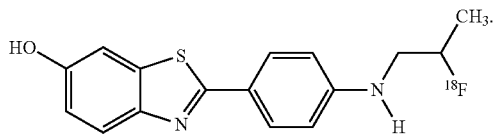 [SMILES: CC([18F])CNc1ccc(-c2nc3ccc(O)cc3s2)cc1]

4. A method for treating a subject suffering from an amyloidosis-associated pathological condition selected from Alzeimer's disease and senile dementia, comprising the step of:
administering a compound, or a pharmaceutical composition comprising the compound and a pharmaceutically acceptable carrier, to the subject;
wherein the compound is

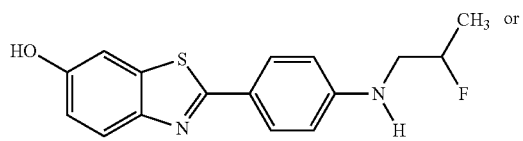

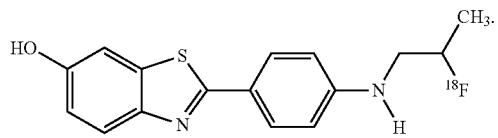

* * * * *